United States Patent
Pang et al.

(10) Patent No.: US 9,783,554 B2
(45) Date of Patent: Oct. 10, 2017

(54) LANTHANIDE ION COMPLEXES AND IMAGING METHOD

(71) Applicants: Yi Pang, Copley, OH (US); Qinghui Chu, Solon, OH (US)

(72) Inventors: Yi Pang, Copley, OH (US); Qinghui Chu, Solon, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 15/186,984

(22) Filed: Jun. 20, 2016

(65) Prior Publication Data
US 2016/0333028 A1    Nov. 17, 2016

Related U.S. Application Data

(62) Division of application No. 13/128,766, filed as application No. PCT/US2009/067684 on Dec. 11, 2009.

(60) Provisional application No. 61/122,850, filed on Dec. 16, 2008.

(51) Int. Cl.
| | |
|---|---|
| A61K 49/00 | (2006.01) |
| C07F 5/00 | (2006.01) |
| C09K 11/06 | (2006.01) |

(52) U.S. Cl.
CPC .......... C07F 5/003 (2013.01); A61K 49/0021 (2013.01); C09K 11/06 (2013.01); C09K 2211/1033 (2013.01); C09K 2211/182 (2013.01)

(58) Field of Classification Search
CPC ...................................................... C07F 5/003
USPC ............................................................ 424/9.2
See application file for complete search history.

(56) References Cited

U.S. PATENT DOCUMENTS 7,105,680 B1 * 9/2006 O'Halloran .......... C07D 263/57
546/271.7

OTHER PUBLICATIONS

Chu et al. Chem. Mater. 2007, 19, 6421-6429.*
Holler et al. J. Photochem. Photobiol. A: Chem. 2002, 149, 217-225.*

* cited by examiner

*Primary Examiner* — Michael G Hartley
*Assistant Examiner* — Sean R Donohue
(74) *Attorney, Agent, or Firm* — Renner Kenner Greive Bobak Taylor & Weber

(57) ABSTRACT

A lanthanide complex, method of forming and method of using the lanthanide complex as a near-infrared luminescent material are described. The complex includes at least one lanthanide ion and at least one polydentate ligand derived from a molecule having the general formula of Structure 2:

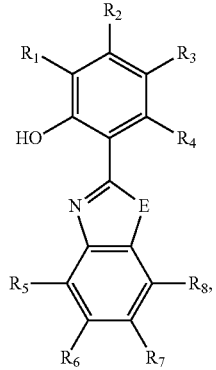

Structure 2 where: E represents a heteroatom or heteroatom-containing group and $R_1$-$R_8$ are independently selected from H, —OH, —$NH_2$, —$SO_3H$, —$CO_2H$, halides, optionally substituted organic groups; and conjugated linking groups which link two of the polydentate ligands of Structure 2 together.

9 Claims, 9 Drawing Sheets

LANTHANIDE ION COMPLEXES AND IMAGING METHOD

CROSS-REFERENCE TO RELATED APPLICATIONS

This application claims priority to co-pending U.S. patent application Ser. No. 13/128,766, filed May 11, 2011, which is a national stage filing of PCT/US09/67684, filed Dec. 11, 2009, which claims priority from U.S. Prov. App. No. 61/122,850, filed Dec. 16, 2009 all of which are incorporated herein by reference.

BACKGROUND

The present exemplary embodiment relates to lanthanide ion complexes. It finds particular application in conjunction with complexes that absorb or fluoresce in the visible or near-infrared (NIR) region of the electromagnetic spectrum, a process for preparing such complexes, and their NIR emission properties that render the complexes useful in imaging applications such as methods of imaging or therapy using such complexes. However, it is to be appreciated that the present exemplary embodiment is also amenable to other like applications.

Imaging techniques are used for a variety of applications, including drug discovery and preclinical testing, studies of disease, treatment and medical diagnosis. Molecular imaging is a rapidly emerging field, as it provides noninvasive visual quantitative representations of fundamental biological processes (T. F. Massoud, S. Gambhir, "Integrating noninvasive molecular imaging into molecular medicine: an evolving paradigm," *Trends in Molecular Medicine* 2007, 13, 183-191). Molecular imaging differs from conventional diagnostic imaging in that it uses probes known as biomarkers, which interact chemically with their surroundings and give signals according to molecular changes/response occurring within the area of interest. This ability to image fine molecular changes can directly or indirectly reflect specific cellular and molecular events that can reveal pathways and mechanisms responsible for disease (R. Weissleder, V. Ntziachristos, "Shedding light onto live molecular targets," *Nature Medicine* 2003, 9, 123-128). It is assumed that molecular probes/markers may serve as early indicators of a disease process, long before a pathomorphological transformation of tissue occurs. Applications include visualization of biodistribution of drugs/ligands, of cell migration for evaluating cell therapies, and the expression of drug targets (receptors, enzymes).

Recently, there has been an increasing interest in identifying luminescent chemosensors for medical diagnostic applications (See, for example, J. Zhang, R. E. Campbell, A. Y. Ting; R. Y. Tsien, "Creating new fluorescent probes for cell biology," *Nature Reviews. Molecular Cell Biology* 2002, 3, 906-918). Some of the reasons for the interest are that luminescence-based imaging is non-invasive, involves non-ionizing radiation, and can provide high sensitivity, thus combining some of the best qualities of PET (positron emission tomography), SPECT, ultrasound, and MRI. Optical imaging uses the fluorescence as optical contrast. Like ultrasound, optical imaging does not have strong safety concerns in comparison with the other medical imaging modalities, which is a valuable attribute (E. M. Sevick-Muraca, J. C. Rasmussen, "Molecular Imaging with Optics: Primer and Case for Near-Infrared Fluorescence in Personalized Medicine," *Journal of Biomedical Optics* 2008, 13, 041303-1-041303/16).

There has been some progress in the design and synthesis of fluorescent probes, enabling detection and imaging of molecular events in various disease conditions such as cancer and vascular pathophysiology. (See, for example, S. Achilefu, "Lighting up Tumors with Receptor-Specific Optical Molecular Probes," *Technology in Cancer Research & Treatment* 2004, 3, 393-409; and J. Klohs, et al., "Near-infrared fluorescent probes for imaging vascular pathophysiology," *Basic Research in Cardiology* 2008, 103, 144-151).

Fluorescent molecules that absorb and emit light in the near-infrared (NIR) region are of particular interest for potential in vivo imaging applications. For biological tissues, the spectral range of interest is approximately 850-1100 nm, where the background noise arising from the fluorescence of the biological material itself (cellular autofluorescence) noise is minimal. During fluorescence microscopy, the fluorophores are subject to photo-irradiation and detectability is limited by cellular autofluorescence and auto-absorption. One approach to overcoming the autofluorescence problem is to develop fluorescent probes that display long emission wavelengths, long decay times, and high quantum yield and high fluorescence brightness (see, for example, Z. Gryczynski, et al., Long-wavelength long-lifetime luminophores for cellular and tissue imaging. In *Proceedings of SPIE, Volume 5323: Multiphoton Microscopy in the Biomedical Sciences*; P. T. C. So, ed. 2004; pp 88-98).

The use of lanthanide chelates as luminescent labels has been increasingly recognized as a technique for detecting biomolecules with high sensitivity. One feature of lanthanide chelate luminescence is that the excited state lifetime is unusually long (often over 1 millisecond) in comparison with the lifetime of organic fluorescent compounds. Therefore, time-resolved fluorometric measurement of lanthanide chelate compounds eliminates the undesired background fluorescence, which decays within several nanoseconds. Other attractive features of lanthanide chelates are their emission in the NIR region, narrow emission bands which originate from the f-f transition of the lanthanide atom, and high detection sensitivity.

The lanthanide elements (abbreviated herein as Ln) are considered to be the sequence of 15 elements with atomic numbers from 57 (lanthanum) to 71 (lutetium). All lanthanide elements are f-block elements, corresponding to the gradual filling of the 4f electron shell. The characteristic f→f transitions are quite narrow, and substantially unaffected by the chemical environment of the ion. These transitions are easily recognizable, making lanthanide ions candidates for optical probes. Most of the lanthanide cations are luminescent, either fluorescent (e.g., $Pr^{3+}$, $Nd^{3+}$, $Ho^{3+}$, $Er^{3+}$, and $Yb^{3+}$) or phosphorescent (e.g. orange $Sm^{3+}$, red $Eu^{3+}$, green $Tb^{3+}$, and blue $Tm^{3+}$). Their emission colors cover the entire spectrum from UV-visible to near-infrared (NIR) region (300-2200 nm). The f-f transitions, however, have low absorption coefficients (smaller than $10\ M^{-1}\ cm^{-1}$), since the electric dipole selection rules forbid such a transition. This hampers the use of lanthanide ions in imaging. In a lanthanide ion complex, however, interaction between the 4f orbitals and the surrounding ligand orbitals provides a mechanism for the energy transfer from the binding ligand (at the excited states) to the lanthanide ions. This indirect excitation process, termed sensitization or antenna effect, can excite the lanthanide ions, which then give NIR emission. To be used in the sensitization, the ligands need to provide efficient energy transfer to the Ln(III) ions.

Among the promising ligands used for NIR sensitization of Ln(III) are 8-hydroxyquinoline derivatives (See, for example, U.S. Pat. No. 6,277,841; and *Inorg. Chem.* 45, 732-743 (2006), *Chemistry—A European Journal* 13, 936-944, (2007)), substituted 2-quinolinols (see, for example, U.S. Pat. No. 7,297,690), porphyrin derivatives (*Coordination Chemistry Reviews* 251, 2386-2399 (2007), and tropolonate ligands (see, for example, J. Zhang, P. D. Badger, S. J. Ceib; S. Petoud, *Angew. Chem, Int. Ed.* 2005, 44, 2508-2512).

However, NIR signals generated with such ligands can be weak and can be masked by autofluorescence signals in imaging.

There remains a need for lanthanide complexes with long decay times which are readily detectable from their luminescence properties.

BRIEF DESCRIPTION

In accordance with one aspect of the exemplary embodiment, a lanthanide complex comprising at least one lanthanide ion and at least one polydentate ligand derived from a molecule having the general formula of Structure 2:

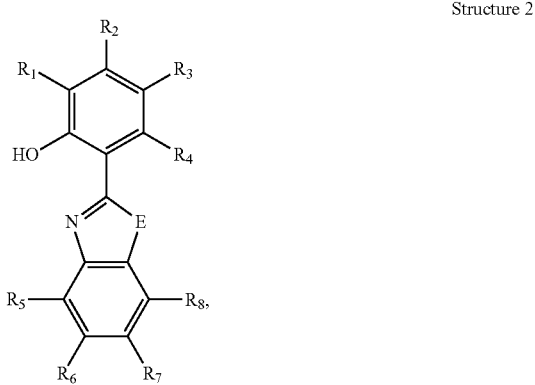

Structure 2 where: E represents a heteroatom or heteroatom-containing group; and $R_1$-$R_8$ are independently selected from H; —OH; —SO$_3$H; —CO$_2$H; —NH$_2$; X, where X represents a halide; optionally substituted organic groups; and conjugated linking groups which link two of the polydentate ligands of structure 2 together.

In accordance with another aspect, a method of forming a lanthanide complex comprising combining a lanthanide ion with a ligand-forming molecule having the general formula of Structure 2:

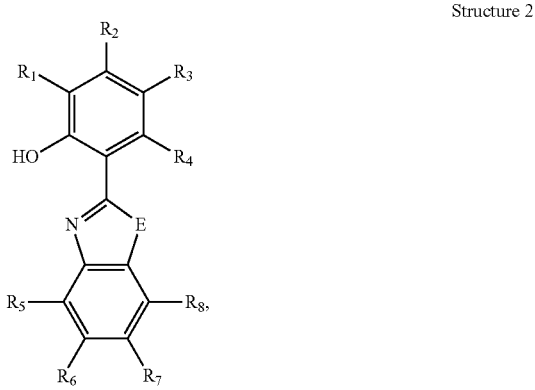

Structure 2 where: E represents a heteroatom or heteroatom-containing group and $R_1$-$R_8$ are independently selected from H; —OH; —SO$_3$H; —CO$_2$H; —NH$_2$; X, where X represents a halide; and optionally substituted organic groups.

DETAILED DESCRIPTION

Figure 1:
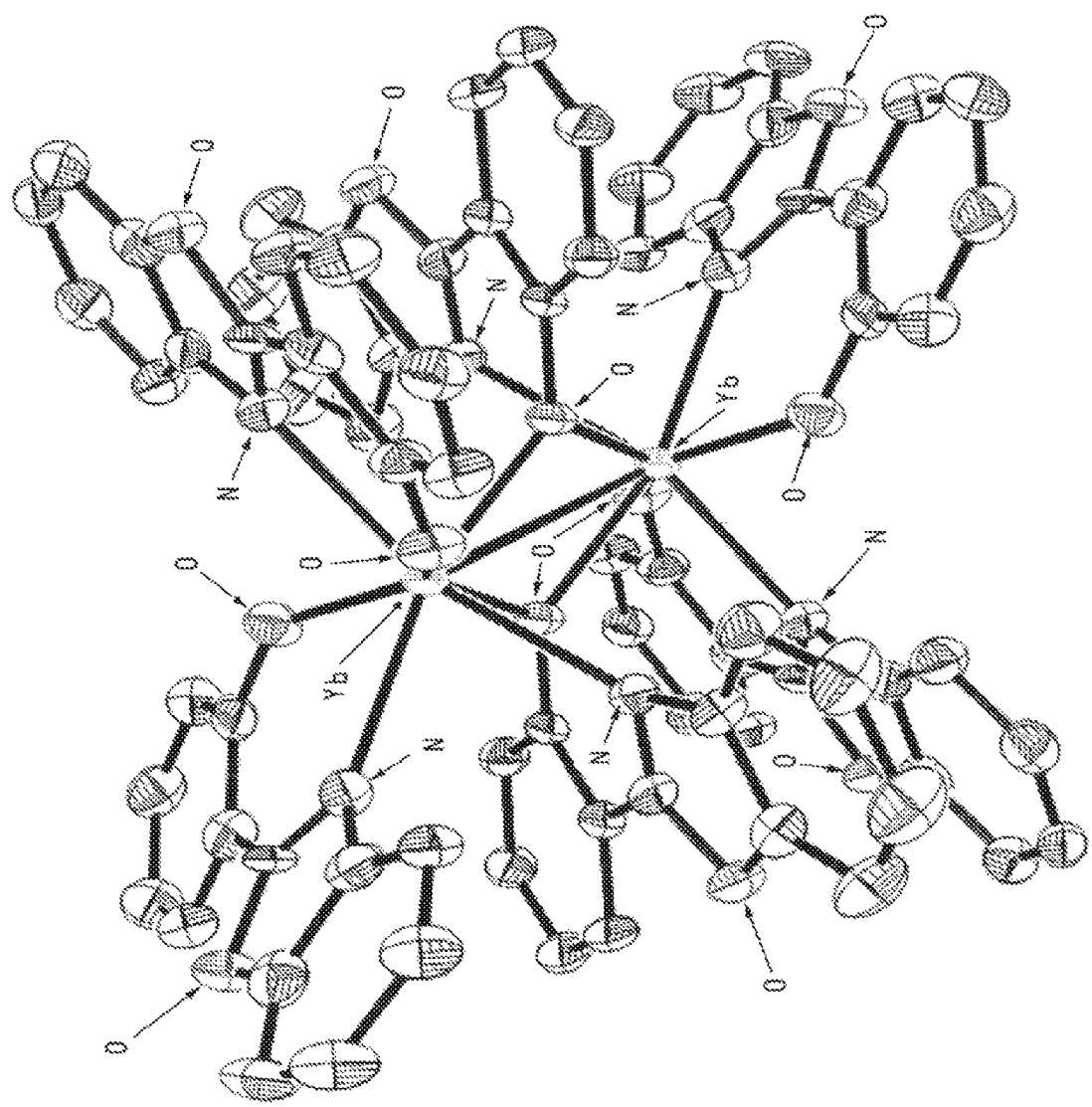
FIG. 1 illustrates an x-ray structure of a representative lanthanide complex of Yb$_2$(HBO)$_6$.

Aspects of the exemplary embodiment relate to a composition comprising a lanthanide ion complex, to a method of forming the complex, and to a method of using the complex which utilizes the luminescent (e.g., fluorescent) properties of the complex. The lanthanide complex includes at least one lanthanide ion and at least one negatively charged ligand L$^1$. The negatively charged ligand L$^1$ is derived from an optionally substituted, 2-(2'-hydroxyphenyl)benzene-fused azole compound, where the azole ring includes, in addition to nitrogen, a hetero atom or group E. E can be O, S, P, Si, B or an N-containing hetero group. Example ligands include ligands of 2-(2'-hydroxyphenyl)benzoxazole (HBO), where E represents oxygen, 2-(2'-hydroxyphenyl)benzothiazole (HBT), where E represents sulfur, and 2-(2'-hydroxyphenyl)benzimidazole (HBI), where E represents N—H, and substituted derivatives thereof. Compounds including such complexes may be in solid or solution form.

It has been found that ligands L$^1$ of this class can chelate with various lanthanide ions to form stable complexes. The exemplary ligands have significant absorption coefficients, appropriate triplet state energy levels that match the energy levels of lanthanide f-orbitals, and a suitable structure to form polydentate chelation with lanthanide ions (through the hydroxyl group of the phenyl and the nitrogen of the azole).

The exemplary ligands can provide improved sensitizing capacity for the lanthanide ions and increased NIR signals, when compared with existing ligands. One reason for the improvement may be that the sensitizing molecule (here, ligand $L^1$) is closer to the $Ln^{3+}$ ion than in existing complexes, thus allowing for more efficient energy transfer.

The exemplary complex may be in the form of a compound represented by the general formula of Structure 1.

Structure 1

In Structure 1, $L^1$, as mentioned above, represents the negatively charged ligand, and will be described in further detail below.

$M^+$ represents an optional monovalent cation. Exemplary monovalent cations include $Li^+$, $NH_4^+$ and combinations thereof.

Ln represents a lanthanide ion. Lanthanide ions are ions of lanthanide elements (now referred to as lanthanoids in IUPAC terminology) which include La, Ce, Pr, Nd, Pm, Sm, Eu, Gd, Tb, Dy, Ho, Er, Tm, Yb, and Lu. Exemplary lanthanide ions include $Pr^{3+}$, $Nd^{3+}$, $Sm^{3+}$, $Dy^{3+}$, $Ho^{3+}$, $Er^{3+}$, $Tm^{3+}$ and $Yb^{3+}$.

A represents an optional anionic ligand. Exemplary anions which may be used as the anionic ligand include those which are capable of forming a soluble salt of a lanthanide element. Exemplary anions include halides, such as $Cl^-$, $AcO^-$, $CF_3SO_3^-$, nitride, and combinations thereof.

$L^2$ represents an optional neutral ligand, examples of which are provided below.

In Formula 1, m, n, p, q, and z each represent a number where n and p are independently at least 1 and m, q, and z, can independently be 0 or greater. Values of m, n, p, q, and z can be selected to provide a charge balanced compound in which each lanthanide ion does not exceed its maximum coordination of 8. Each $L^1$ ligand is polydentate and occupies two (or more) of these coordination sites. In the case where $L^1$ is a bidentate ligand $(L^1)^-$, for example, the remaining ligands q, and z are limited to a maximum of 6n. In one embodiment, for example, p=3n+m−q. Exemplary values are as follows: m=0,1; n=1,2; p=1-6; e.g., p=1,2; z=0,1; q=0 to (3n−p). In some instances, $L^1$ has a valency of greater than 1, e.g., is a divalent anion, in which case, the values of m, n, p, q, and z may be appropriately selected accordingly.

$L^1$ may be a polydentate ligand derived from a molecule having the general formula represented by Structure 2.

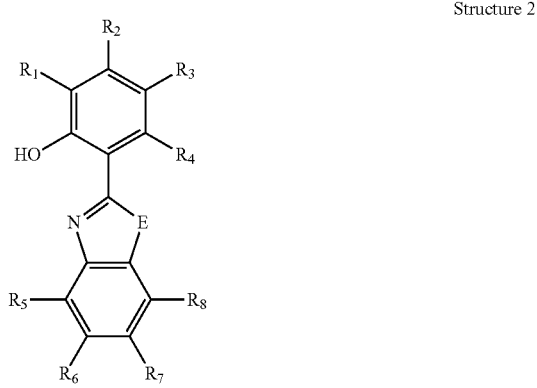

Structure 2

E represents a heteroatom or heteroatom-containing group. Exemplary heteroatoms/groups include O (oxygen), S (sulfur), P (phosphorus), B (boron), Si (silicon) and N—R, where R represents a stabilizing group, such as H, alkyl, aryl, or the like, e.g., of from 1 to about 6 carbon atoms. In specific embodiments, E is selected from O, S, and N—R. In one specific embodiment, R is H or $CH_3$. The E group or atom is an electron donating group which helps to stabilize the 5-membered azole ring and give it aromatic character. The E group affects the emission characteristics, as discussed below. R and $R_1$-$R_8$ may be independently selected from H; —OH; —$SO_3H$; —$NH_2$; —$CO_2H$; X, where X represents a halide; and organic groups, e.g., optionally substituted $C_1$-$C_{30}$ groups selected from alkoxy (—$OR_9$), amino (e.g., —NHR', —NR'R") and alkyl amino (e.g., —R'"NHR', —R'"NR'R"); alkyl, alkenyl, alkynyl, cycloalkyl, aryl, alkylaryl, heterocyclic groups, ring structures formed by two or more of $R_1$-$R_8$; and combinations thereof. R', R" and $R_9$ can be selected from optionally substituted $C_1$-$C_{15}$ groups selected from alkyl, alkenyl, alkynyl, cycloalkyl, aryl, and alkylaryl; R'" can be an optionally substituted alkyl bridging group of up to three carbon atoms in length; and one or more of $R_1$-$R_8$ may be a linking group which links two such ligands $L^1$. In general these groups are not destabilizing in the complex.

By polydentate, it is meant that the ligand provides two or more coordination sites for the lanthanoid ion. In general, each of these coordination sites is associated with a different ring of the ligand.

Exemplary halides X in the above can include Cl and Br.

Exemplary $C_1$-$C_{15}$ heterocyclic groups suited to use as R and $R_1$-$R_8$, and in particular, for $R_1$, include optionally substituted groups such as

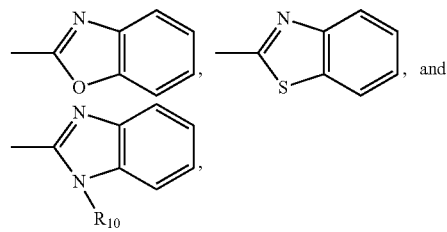

where $R_{10}$ can be as described above for $R_9$.

In all the above, "optionally substituted" means that the group in question can include a substituent for one or more of its hydrogen or carbon atoms, such as alkyl, aryl, alkoxy, aryloxy, a heteroatom containing substituent, X, O, S, N or the like.

For example, an amino/alkyl amino can be represented by —$(C)_n$NR'R", where R" can be as for R' and the carbon containing group $(C)_n$ represents an optional short alkyl bridging group (R'") which links the amino group to the complex. For example n=0 (i.e., no alkyl bridge), 1 (e.g., —$CH_2$—), or 2 (e.g., —$CH_2$—$CH_2$—). As specific examples of substituted amino/alkylamino groups, $R_1$ and/or $R_5$ is independently a metal-chelating group such as a dipicolyl amino (DPA)-containing group or a polyaminocarboxylic acid-containing group. A polyaminocarboxylic acid-containing group is a group containing one or more nitrogen atoms connected through one or more carbon atoms to one or more carboxyl groups, and wherein the nitrogen is optionally linked to the complex via an alkyl bridge. A dipicolyl amino (DPA)-containing group includes a nitrogen atom connected to two, optionally substituted, 2-pyridinemethane groups, and wherein the nitrogen is optionally linked to the complex via an alkyl bridge. Examples of these groups where n=1 are shown below.

Exemplary polyaminocarboxylic acid-containing group:

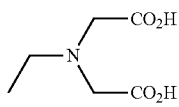

Exemplary dipicolyl amino-containing group:

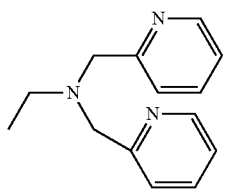 [SMILES: CCN(Cc1ccccn1)Cc1ccccn1]

Such groups, particularly at the $R_1$ and $R_5$ positions, are useful chelating groups and thus may be useful in tuning the ion-binding properties of the complex. Another useful chelating group for the $R_1$ and/or $R_5$ positions is —COOH.

In one embodiment, when $R_1$-$R_8$ are all H, and E is respectively, O, S, and N—H, Structure 2 corresponds respectively to 2-(2'hydroxyphenyl)benzoxazole (HBO), 2-(2'-hydroxyphenyl)benzothiazole (HBT), and 2-(2'-hydroxyphenyl)benzimidazole (HBI). Exemplary neutral ligands $L^2$ in Structure 1 include, but are not limited to:

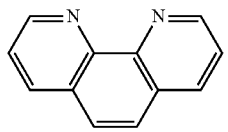 [SMILES: c1cnc2c(c1)ccc1cccnc12]

(1,10-phenanthroline),

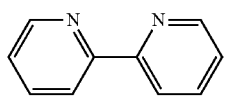 [SMILES: c1ccc(-c2ccccn2)nc1]

(bipyridine),

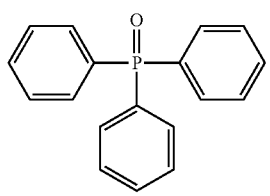 [SMILES: O=P(c1ccccc1)(c1ccccc1)c1ccccc1]

(triphenylphosphine oxide or TPPO),

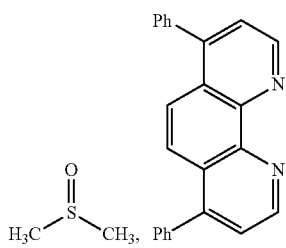

(Bathophenanthroline or Bphen), $H_2O$, and combinations and optionally substituted derivatives thereof.

In the case where $L^1$ is bidentate (monovalent), the complex may have the general formula of Structure 3:

Structure 3

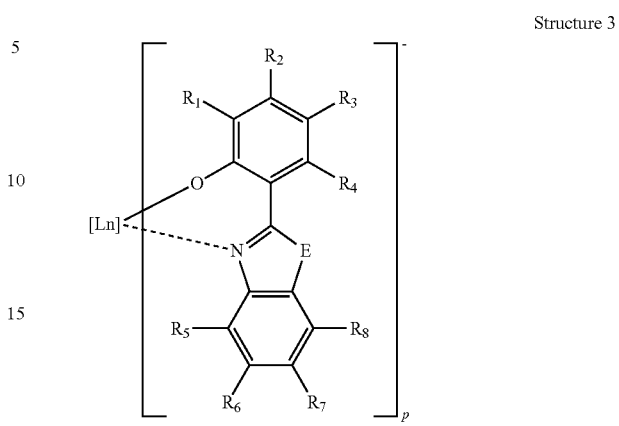

In this case, the compound may be represented by Structure 4:

Structure 4

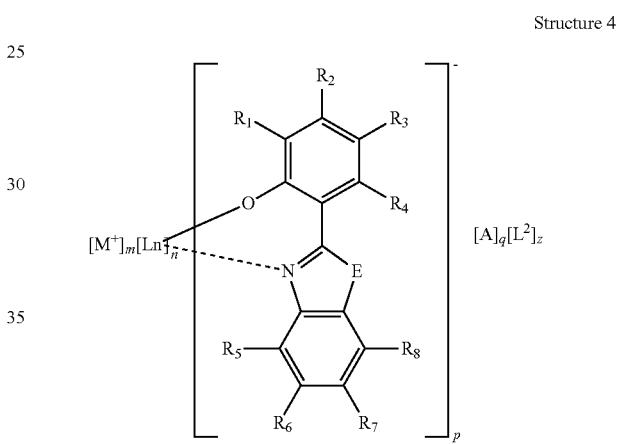

As can be seen, the bidentate ligand $L^1$ in Structure 4 is formed by removal of hydrogen from Structure 2. An ionic bond forms between $L_n$ and O on the ligand, with the closely positioned N on the heterocycle occupying a second coordination site through a non-ionic bond.

Specific examples of ligand $L^1$ (shown in their neutral form) are shown in Structures 5-13:

A. Derivatives of HBO:

Structure 5

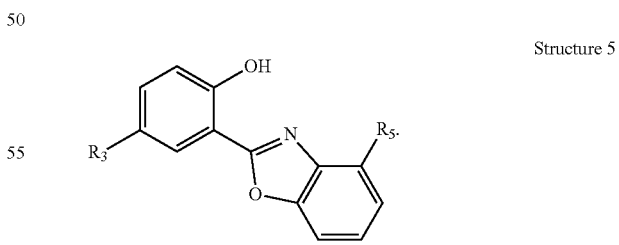

For example, $R_3$=H, X, —$OR_9$, —NHR' or $CH_3$ and/or $R_5$=—H,

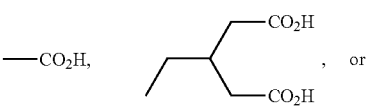

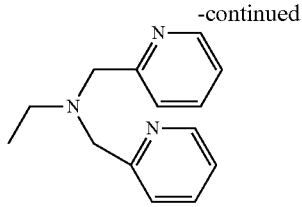

Structure 6

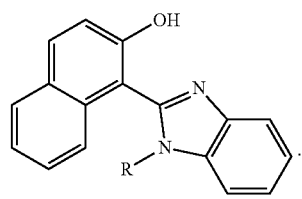

Structure 12

For example, R=H or CH$_3$

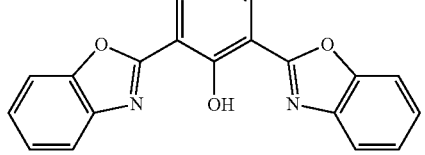

Structure 7

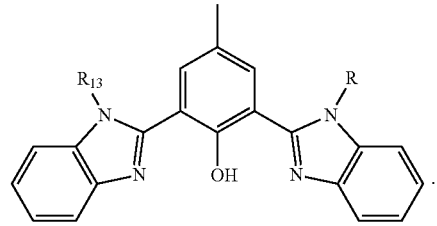

Structure 13

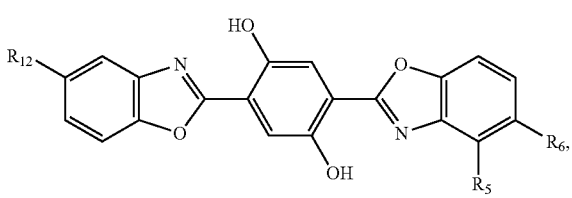

where R$_{12}$ can be as for R$_6$, e.g., R$_{12}$=H or C(CH$_3$)$_3$ and R$_6$=H or C(CH$_3$)$_3$. In one embodiment, R$_{12}$=R$_6$. R$_5$ can be as described above for structure 5.

B. Derivatives of HBT:

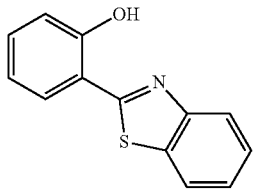

Structure 8

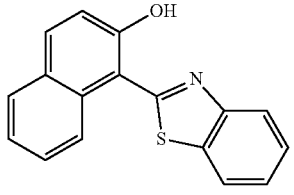

Structure 9

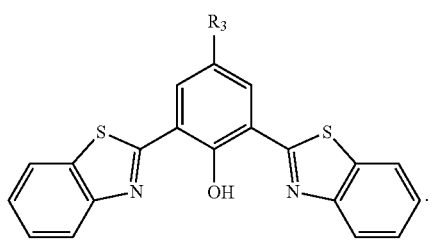

Structure 10

For example, R$_3$=X or CH$_3$
Derivatives of HBI:

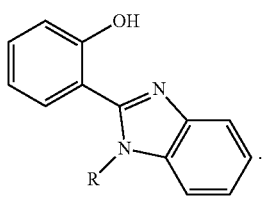

Structure 11

For example, R=H or CH$_3$

For example, R=H or CH$_3$ and R$_{13}$=H or CH$_3$. In one embodiment, R$_{13}$=R In the case where L$^1$ has at least two metal bonding sites, L$^1$ may have the general formula of Structure 14:

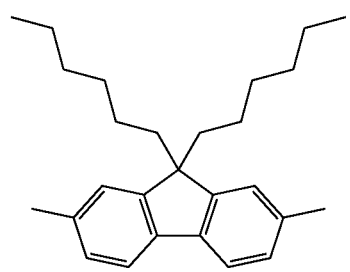

Structure 14 where E and E' can independently be as for E above;

R$_{14}$ and R$_{15}$ each represent a substituent independently selected from R$_1$, R$_2$, and R$_4$ as above, i.e., in the R$_1$, R$_2$, and/or R$_4$ position, e.g., both may be in the R$_1$ position; and R$_{16}$ represents a conjugated linking group, such as one of structures 15 and 16:

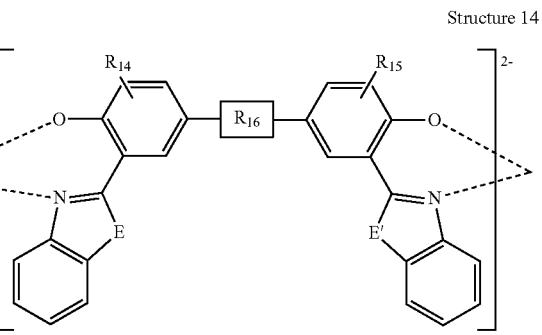

Structure 15

Structure 16
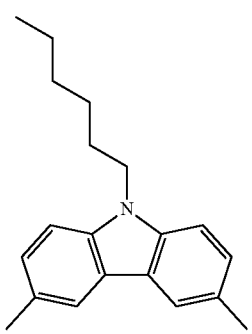
Structure 18
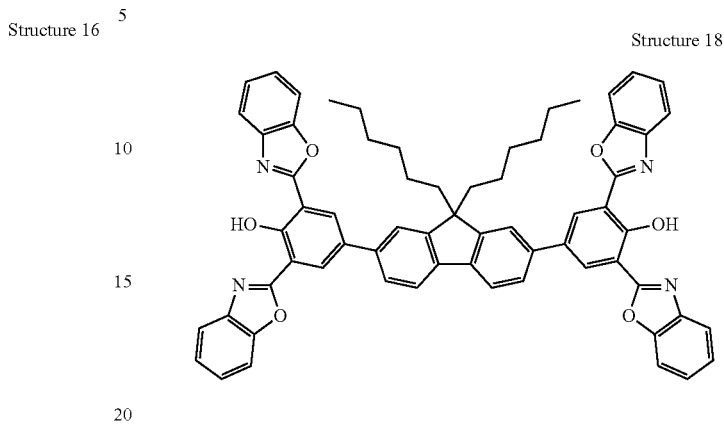
Examples of divalent (quatrodentate) ligands $L_1$ (shown in their neutral form) are illustrated in Structures 17-19:
Structure 19
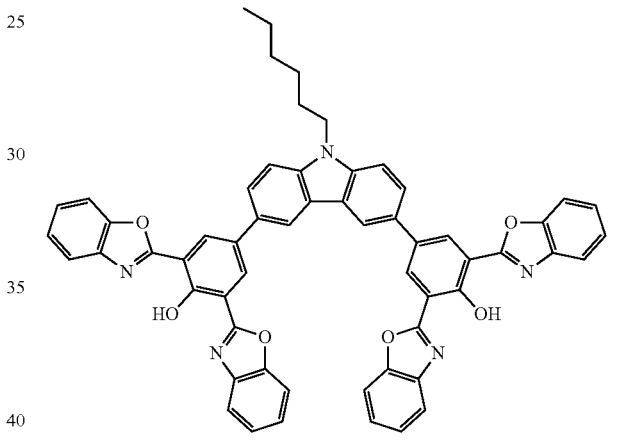
Structure 17
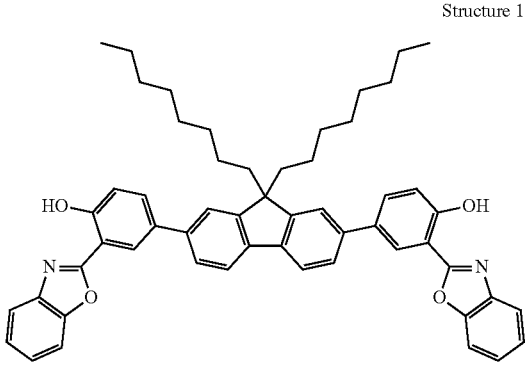
In one embodiment, the structure of the complex comprising the ligand of Structure 14 can be represented by Structure 20:
Structure 20
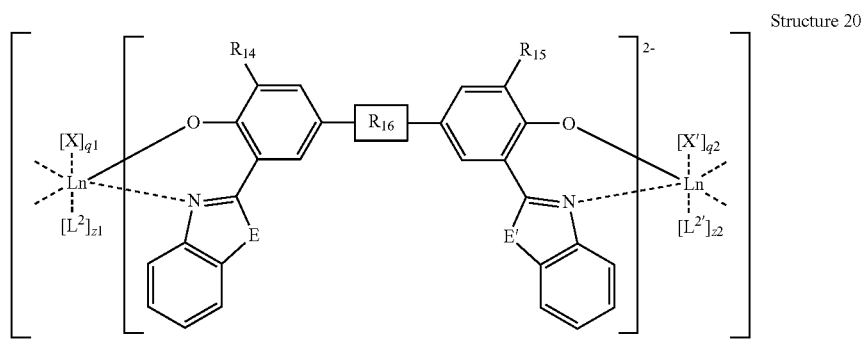

where $L^{2'}$ and $L^2$ may be independently selected from neutral ligands, as for $L^2$ above; and $X'$ and $X$ may be independently selected from anions, as for $X$ above;

$q_1$ and $q_2$ may be as for q;

$z_1$ and $z_2$ may be as for z.

In another embodiment, the composition may be a polymer of the general form shown in Structure 21:

Structure 21

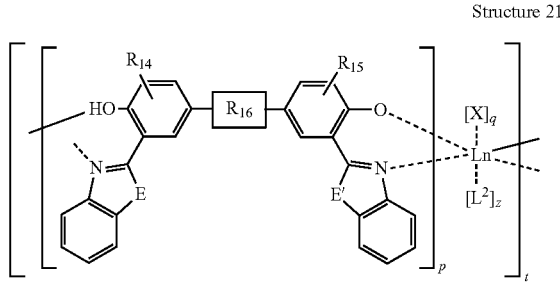

where $R_{14}$-$R_{16}$ are as described above and t can be an integer which is e.g., from 2-100.

The exemplary complexes and compounds comprising them can be used as effective photosensitizers for lanthanide ions. In particular HBI derivatives have been found to form NIR luminescent complexes with eight lanthanide ions (Pr, Nd, Sm, Dy, Ho, Er, Tm, and Yb). HBO and HBT derivatives have been found to form NIR luminescent complexes with six lanthanide ions (Pr, Nd, Sm, Ho, Er, and Yb). In general, the relative luminescent intensity of the resulting complexes follows the general trend HBT>HBO>HBI complexes.

The exemplary compositions are suitable for use with a variety of other modalities including X-rays, magnetic resonance, and radiographic imaging.

Electron donating and electron releasing groups at various positions in the ligands of Structures 1 and 2 provide an opportunity to alter the absorption and emission properties of the complex thereby enhancing the optical utility of these molecules. Also, these additional functionalities afford the capability of conjugation of the exemplary complexes and compounds to biomolecules and synthetic polymers for selective delivery to various organs or tissues of interest. The term biomolecule' refers to all natural and synthetic molecules that play a role in biological systems. Biomolecules include hormones, amino acids, peptides, peptidomimetics, proteins, nucleosides, nucleotides, nucleic acids, carbohydrates, lipids, albumins, mono- and polyclonal antibodies, receptor molecules, receptor binding molecules, and aptamers. Specific examples of biomolecules include inulins, prostaglandins, growth factors, growth factor inhibitors like somatostatin, liposomes, and nucleic acid probes. Examples of synthetic polymers include polylysine, polyaspartic acid, polyarginine, aborols, dendrimers, and cyclodextrins. Coupling of such complexes to biomolecules can be accomplished by several known methods (see, for example, Hnatowich, et al., Science, 1983, 220, 613).

The exemplary complexes thus find application in a variety of imaging techniques of which the following are examples:

1. Detection of diseases. For this application, the complex may serve as a reporter for a targeting biomolecule which is specific for the disease. A probe comprising the complex and a coupled targeting biomolecule is introduced to the body of a human or other animal subject, e.g. as a pill or liquid to be swallowed, or by injection. Due to the targeting biomolecule, the probe concentrates in regions of diseased cells, such as cancer cells. When energized, e.g., by illuminating the subject with radiation in the visible region of the spectrum, the exemplary complex luminesces. A detector is positioned proximate the subject. The detector detects the emitted radiation in a selected NIR range at which the luminescence occurs. The detector sends signals to a reconstruction processor which generates an image of the subject or portion of the subject, based on the received signals. In general, such images use color or grayscale to indicate the determined concentration of the luminescing complex.

Using a hybrid detection technology, the image can be superimposed over or otherwise combined with a second image which shows features of the body, such as organs, bone or tissue. The second image can be generated by another imaging technique, such as positron emission spectroscopy (PET), (SPECT), or magnetic resonance imaging (MRI). The exemplary complex-containing probe can be administered along with a marker for the second imaging technique. Or, the hybrid image may be generated by detecting luminescence at two wavelengths, one for the complex, the other selected for detecting auto-luminescence from the body.

The exemplary complex allows early detection of diseases, even at the molecular level. Such techniques can be used to detect whether a subject has a particular disease or to follow the progress of a disease.

2. Identifying candidate treatments of diseases. In this embodiment, a probe includes the complex linked to a candidate therapeutic agent, such as a drug. The ability of the drug to target a known disease site, such as a cancer, can be tracked by the complex. The complex acts as a reporter for the drug movement, in a similar manner to that described for detection. If the detected concentration of the complex at the known disease site is higher than in surrounding tissue, it can be inferred that the candidate therapeutic agent is specific for the disease site 3. Treatment. Certain drugs and other therapeutic agents are harmful and it is desired to use the minimum needed to treat the disease site. By linking the complex to a therapeutic agent, as in 2, above, the amount of therapeutic agent at the disease site can be determined, as a function of the fluorescence detected. An appropriate dosage can then be determined for achieving a desired concentration of the therapeutic agent at the disease site.

To form diagnostic compositions comprising the exemplary compounds and probes containing them, an effective amount of one or more of the exemplary compounds alone or in the form of a probe may be dispersed in a pharmaceutically acceptable composition and administered to a patient either systemically or locally to the organ or tissue to be studied. These compositions may also include stabilizing agents, such as amino acids, peptides and mono- or polycarboxylic acids, amines, nucleotides, or saccharides. For example, parenteral administration advantageously contains a sterile aqueous solution or suspension of the complexe(s) whose concentration ranges from about 1 nM to about 0.5 M. For example, the complex may be present in the pharmaceutical composition at a concentration of at least 0.1% by weight and up to about 90% by weight.

Such solutions also may contain pharmaceutically acceptable buffers, emulsifiers, surfactants, and, optionally, electrolytes, such as sodium chloride. Such enteral compositions may optionally include buffers, surfactants, emulsifiers, thixotropic agents, and the like. Compositions for oral administration may also contain flavoring agents and other ingredients for enhancing their organoleptic qualities. The diagnostic compositions are administered in doses effective to achieve the desired diagnostic or therapeutic objective. Such doses may vary widely depending upon the particular complex employed, the organs or tissues to be examined, the equipment employed in the clinical procedure, and the like.

The complex also finds application in telecommunication applications, for example, in a transmitting material such as an optical fiber. It may also find application in lasers and as a light emitting material, for example, in a light emitting diode (LED). In an LED, for example, a layer comprising the complex may be excited by electrical current and emit light at a wavelength, e.g., in the visible or Near-IR region. Preparation of Near-IR Emitting Materials Comprising the Complex:

A. Heterogeneous Reaction

Scheme 1 illustrates exemplary methods for synthesis of near infrared-emitting materials in a heterogeneous reaction.

In reaction C, a complex of the form $MLnL^1_4$ can be formed as a precipitate by reaction of a lanthanide salt $LnX_3$ (e.g., a lanthanide chloride), with a ligand $L^1$ and a cation $M^+$, as described above, e.g., in the form of a base, MOH. The reaction can be conducted in a suitable solvent, such as ethanol, at a suitable reaction temperature, such as room temperature.

In reaction D, a complex of the form $LnL^1_3 \cdot DMSO$ can be formed by recrystalization of $Ln_2L^1_6$ (formed in reaction A)

Scheme 1

Heterogeneous Reaction

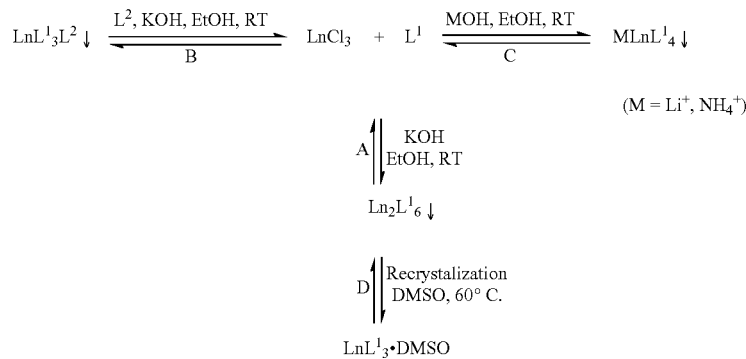

$(M = Li^+, NH_4^+)$

In reaction A, a complex of the form $Ln_2L^1_6$ can be formed by reaction of a lanthanide salt $LnX_3$ (e.g., a lanthanide chloride), with a ligand $L^1$ in neutral form such as any one or more of those illustrated in Structures 5-13 in an approximately 1:3 molar ratio of Ln to $L^1$. The reaction may be carried out in a suitable solvent, such as $C_1$-$C_6$ alcohol, e.g., ethanol or methanol, and optionally also a base capable of reacting with the halide in the lanthanide salt, but which does not tend to complex with the lanthanide ion, such as KOH or NaOH. The reaction generally proceeds at room temperature (e.g., 15-25° C.) to form a precipitate of $Ln_2L^1_6$.

In reaction B, a complex of the form $LnL^1_3L^2$ can be formed as a precipitate by reaction of a lanthanide salt $LnX_3$ (e.g., a lanthanide chloride), with a ligand $L^1$ and a ligand $L^2$; where $L^1$ is in neutral form such as any one or more of those illustrated in Structures 5-13 and $L^2$ can be any neutral ligand. The reactants can be in an approximately 1:3:1 molar proportion of $Ln:L^1:L^2$. The reaction can be conducted in a suitable solvent, such as ethanol, at a suitable reaction temperature, such as room temperature.

in dimethylsulfoxane (DMSO) at a suitable reaction temperature, such as room temperature. Here, DMSO acts as ligand $L^2$.

The following are examples of such heterogeneous reactions which result in solid products.

Example 1: Synthesis of Compound 1 ($Yb_2HBO_6$)

0.2586 g of 2-(2'hydroxyphenyl)benzoxazole (HBO) (1.225 millimoles) and 67 mg of KOH (1.196 mmol) were dissolved in 50 mL of absolute ethanol in a 100 mL flask, to which 0.155 g of $YbCl_3 \cdot 6H_2O$ (0.402 mmoles) in 40 mL of absolute ethanol was added. Upon addition, the precipitate formed immediately, and the mixture was stirred overnight. The precipitate was collected by filtration and washed three times with water and absolute ethanol, respectively. After drying in a vacuum oven at 50° C. for overnight, the product was obtained as a solid (0.16 g), giving a yield of 49.8%.

A single crystal was grown by slow evaporation of the product solution in dimethylformamide (DMF). On the basis of x-ray analysis, the structure of the synthesized complex was determined to be $Yb_2(HBO)_6$ with a structure as shown in Structure 22:

Structure 22

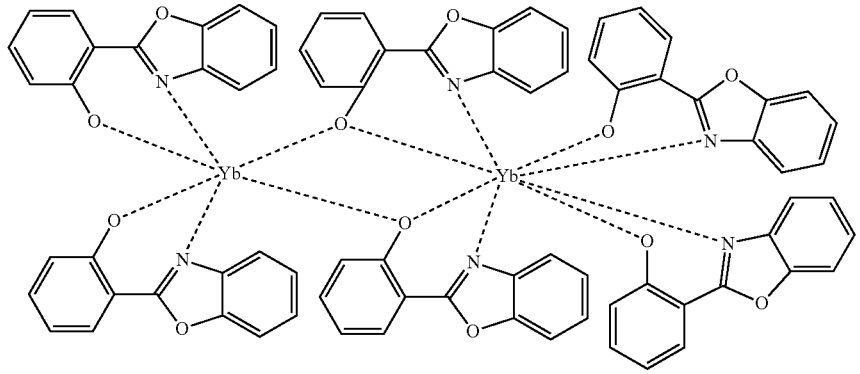

It is anticipated that the lanthanide complexes of Examples 2-5 below may be analogous to Structure 22.

Example 2: Synthesis of Compound 2 ($Er_2HBO_6$)

0.2586 g of HBO (1.225 mmol) and 67.8 mg of KOH were dissolved in 50 mL of absolute ethanol in a 100 mL flask, to which 0.1514 g of $ErCl_3.6H_2O$ (0.3984 mmoles) in 40 mL of absolute ethanol was added. Upon addition, the precipitate was immediately formed, and the mixture was stirred overnight. The precipitate was collected by filtration and washed three times with water and absolute ethanol, respectively. After drying in a vacuum oven at 50° C. overnight, the product was obtained as a solid (0.20 g) in 62.2% yield.

Example 3: Synthesis of Compound 3 ($Sm_2HBO_6$)

0.2586 g of HBO (1.225 mmol) and 67.8 mg of KOH were dissolved in 50 mL of absolute ethanol in a 100 mL flask, to which 0.1027 g of $SmCl_3$ (0.403 mmoles) was added. Upon addition, the precipitate was immediately formed, and the mixture was stirred overnight. The precipitate was collected by filtration and washed three times with water and absolute ethanol, respectively. The resulting solids were dried in a vacuum oven at 50° C. overnight. The product was obtained as a solid (0.25 g) in 80.0% yield.

Example 4: Synthesis of Compound 4 ($Pr_2HBO_6$)

0.2586 g of HBO (1.225 mmol) and 67.8 mg of KOH were dissolved in 50 mL of absolute ethanol in a 100 mL flask, to which 0.1418 g of $PrCl_3.6H_2O$ (0.401 mmol) in 40 mL of absolute ethanol was added. Upon addition, the precipitate was immediately formed, and the mixture was stirred overnight. The precipitate was collected by filtration and washed three times with water and absolute ethanol, respectively. The resulting solids were dried in a vacuum oven at 50° C. overnight. The product was obtained as a solid (0.24 g) in 77.8% yield.

Example 5: Synthesis of Compound 5 ($Nd_2HBO_6$)

0.2586 g of HBO (1.225 mmol) and 67.8 mg of KOH were dissolved in 50 mL of absolute ethanol in a 100 mL flask, to which 0.1423 g of $NdCl_3.6H_2O$ (0.399 mmoles) in 40 mL of absolute ethanol was added. Upon addition, the precipitate was immediately formed, and the mixture was stirred overnight. The precipitate was collected by filtration and washed three times with water and absolute ethanol, respectively. The resulting solids were dried in a vacuum oven at 50° C. overnight. The product was obtained as a solid (0.18 g) in 58.1% yield.

Example 6: Synthesis of Compound 6 ($LiYbHBO_4$)

0.155 g of $YbCl_3.6H_2O$ (0.402 mmoles) was dissolved in 40 mL of absolute ethanol in a 100 mL flask, to which 0.2936 g of HBO (1.391 mmol) and 33.29 mg of LiOH dissolved in 50 mL of absolute ethanol were added dropwise. A precipitate gradually formed as the reactants were added. The mixture was stirred and heated at 60° C. for 3 hrs. The precipitate was collected by filtration and washed three times with water and absolute ethanol, respectively. The resulting solids were dried in a vacuum oven at 50° C. overnight. The product was obtained as a solid (0.26 g) in a 72.2% yield. The composition of the compound was identified by Mass Spectrum.

Example 7: Synthesis of Compound 7 ($YbHBO_3Phen$)

0.2586 g of HBO (1.225 mmol), 0.072 g of 1,10-phenanthroline (Phen) and 28.7 mg of LiOH were dissolved in 50 mL of absolute ethanol in a 100 ml flask and heated at 60° C. To this mixture, 0.155 g of $YbCl_3.6H_2O$ (0.402 mmoles) dissolved in 40 mL of absolute ethanol was added in parts. The precipitate was gradually formed when the reactants were added. The mixture was stirred and heated at 60° C. for 3 hrs. The precipitate was collected by filtration and washed three times with water and absolute ethanol, respectively. The resulting solids were dried in a vacuum oven at 50° C. overnight. The product was obtained as a solid (0.28 g) in a 71.2% yield.

Example 8: Synthesis of Compound 8 ($YbHBO_3Py$)

0.2586 g of HBO (1.225 mmol), 0.062 g of 2, 2'-bipyridine (Py) and 67 mg of LiOH were dissolved in 50 mL of absolute ethanol in a 100 ml flask and heated at 60° C., to which 0.155 g of $YbCl_3.6H_2O$ (0.402 mmoles) in 40 mL of absolute ethanol was added in parts. The precipitate gradually formed when the reactants were added. The mixture was stirred and heated at 60° C. for 3 hrs. The precipitate was collected by filtration, and washed three times with water and absolute ethanol. The resulting solids were dried in the vacuum oven at 50° C. overnight. The product was obtained as a solid (0.29 g) in a 75.5% yield.

Example 9: Synthesis of Compound 9 ($YbHBO_3TPPO$)

0.2586 g of HBO (1.225 mmol), 0.1177 g of triphenylphosphine oxide (TPPO) and 67 mg of KOH were dissolved in 50 mL of ethanol in a 100 ml flask and heated at 60° C., to which 0.155 g of $YbCl_3.6H_2O$ (0.402 mmoles) dissolved in 40 mL of absolute ethanol was added. Upon addition of the reactants, the precipitate immediately formed. The mixture was stirred and heated at 60° C. for 3 hrs. The precipitate was collected by filtration and washed three times with water and absolute ethanol. The resulting solids were dried in a vacuum oven at 50° C. overnight. The product was obtained as a solid (0.16 g) in a yield of 36.5%.

Example 10: Synthesis of Compound 10 ($YbHBO_3Bphen$)

0.2586 g of HBO (1.225 mmol), 0.133 g of Bathophenanthroline (Bphen) and 67 mg of KOH were dissolved in 50 mL of absolute ethanol in a 100 ml flask. To the flask, a solution of 0.155 g of $YbCl_3.6H_2O$ in 40 mL of absolute ethanol was added in parts. Upon addition, the precipitate immediately formed, and the mixture was stirred overnight. The precipitate was collected by filtration and washed three times with water and absolute ethanol. The resulting solids were dried in a vacuum oven at 50° C. overnight. The product was obtained as a solid (0.20 g) in a yield of 44.0%.

Example 11: Synthesis of Compound 11 ($YbHBT_3Bphen$)

0.2727 g of HBT, 0.0199 g of Bphen and 28.7 mg of LiOH were dissolved in 50 mL of absolute ethanol in a 100 ml flask and heated at 60° C., to which 0.155 g of YbCl₃.6H₂O dissolved in 40 mL of absolute ethanol was added in parts. The precipitate gradually formed when the reactants were added. The mixture was stirred and heated at 60° C. for 3 hrs. The precipitate was collected by filtration and washed three times with water and absolute ethanol, respectively. The resulting solids were dried in a vacuum oven at 50° C. overnight. The product was obtained as a solid (0.16 g) in a yield of 33.8%.

Example 12 Synthesis of Compound 12 (YbHBI₃Bphen)

0.2523 g of HBI, 0.199 g of Bphen and 28.7 mg of LiOH were dissolved in 50 mL of absolute ethanol in a 100 ml flask. The mixture was heated to 60° C., and a solution of YbCl₃.6H₂O (0.155 g) in 40 mL of absolute ethanol was added in parts. The mixture was stirred at 60° C. for 3 hrs without observing any precipitation. The solvents were removed using a rotary evaporator. The resulting solids were collected by filtration, washed three times with water and absolute ethanol respectively, and dried in a vacuum oven at 50° C. overnight, giving 0.40 g. This amounts to a yield of 88.3%.

B. Preparation of Near-IR Emitting Materials in Solution:

Scheme 2 illustrates the synthesis of Near IR Emitting Materials by Homogeneous Reaction.

Scheme 2

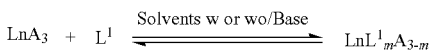

Solvents: MeOH, EtOH, DMSO, and etc.
Base: Net₃, C₅H₅N, and etc.
A = Anions such as Cl⁻, NO₃⁻, AcO⁻, CF₃SO₃⁻, and etc.
m = 1, 2

In reaction scheme 2, lanthanide halide, such as LnCl₃ (or other LnA₃ compound), and ligand L¹ are reacted to form a complex of the general form LnL¹$_m$A$_{3-m}$. The value of m depends on the molar proportions of the starting materials. For example, a ratio of LnA₃:L¹ may be approximately 1:1 to 1:2. The reaction may be conducted in a suitable solvent, such as an alcohol (e.g., methanol or ethanol), or DMSO, and optionally further in the presence of a tertiary amine, such as triethylamine, pyridine, or other nitrogenous base. For example, complexes such as LnL¹₂Cl and LnL¹Cl₂ may be formed in this way. A solution comprising the complex formed by reaction scheme 2 may include the complex at a concentration of at least 1 nanomole (10⁻⁹ mole/liter). In one embodiment, the solution comprises at least 1 wt % of the complex and can comprise up to 90 wt % of the complex.

Example 13: General Procedures for Preparation of Exemplary Complexes in Solution One part of a selected ligand L¹ was dissolved in a solvent selected from methanol, ethanol, DMSO, chloroform, and dioxane. Into this ligand solution, 2-4 parts of a lanthanide salt and, in some cases, triethylamine (NEt₃) were added. The resulting solution turned a slight yellow color with weak fluorescence under UV irradiation (with a UV lamp), and a new peak emerged at a longer wavelength in the UV-Vis absorption spectra. When exciting at the new absorbance wavelength, the solution gave characteristic photoluminescence (PL) in the Near IR region, clearly indicating the coordinating reaction was taking place in the system. Representative results are shown in Tables 1 and 2. For Table 1, L¹ was a ligand derived from structure 6 (a derivative of HBO). For Table 2, L¹ was HBO.

In these tables, ✓ indicates the reaction was completed. ↓ indicates precipitation occurred from the reaction. x indicates no reaction was observed. NIR indicates the complex gave NIR emission. N/A indicates that the combination was not investigated. Ø indicates the reaction occurs partially (or incomplete reaction).

TABLE 1

Coordination Chemistry of a ligand of structure 6 with different lanthanide ions in a variety of solvents with and without triethylamine (NEt₃)

| | MeOH | | EtOH | | DMSO | |
|---|---|---|---|---|---|---|
| Lanthanide ions | Without NEt₃ | With NEt₃ | Without NEt₃ | With NEt₃ | Without NEt₃ | With NEt₃ |
| Yb(AcO)₃ | ✓, NIR | ✓, NIR | ✓, NIR | ✓, NIR | ✓, NIR | ✓, NIR |
| Yb(CF₃SO₃)₃ | ✓, NIR | ↓ | ✓, NIR | ↓ | x | ✓, NIR |
| YbCl₃ | ✓, NIR | ↓ | ✓, NIR | ↓ | x | ✓, NIR |
| NdCl₃ | ✓, NIR | ↓ | ✓, NIR | ↓ | x | ✓, NIR |
| ErCl₃ | ✓ | ↓ | ✓ | ↓ | x | ✓, NIR |

As can be seen from Table 1, each of the lanthanide ions shown formed a complex and exhibited fluorescence in at least one of the solvents tested. In the case of alcohols as the solvent, the complexation can proceed completely without the promotion of triethylamine, indicating the strong likelihood of coordinating ability of the ligand of structure 6. It is suggested that its Y-type geometry structure is favorable for entropy driven complexation. The complexation of several lanthanide ions was also tested in chloroform and dioxane, both with and without NEt₃, but no reaction took place. Moreover, the addition of triethylamine is advantageous for the complete reaction in the case of DMSO, reflecting the impact of solvent and base on the complexation.

TABLE 2

Coordination Chemistry of HBO with different lanthanide ions in a variety of combinations of solvents and triethylamine

| | MeOH | | DMSO | | Dioxane | |
|---|---|---|---|---|---|---|
| Lanthanide ions | Without NEt₃ | With NEt₃ | Without NEt₃ | With NEt₃ | Without NEt₃ | With NEt₃ |
| Yb(AcO)₃ | Ø | Ø NIR | ✓ NIR | ✓ NIR | x | x |
| YbC₃ 6H₂O | Ø | ✓ NIR | Ø | ✓ NIR | x | x |
| NdCl₃ 6H₂O | x | ✓ NIR | x | ✓ NIR | x | x |
| ErCl₃ 6H₂O | Ø | ✓ | Ø | ✓ NIR | x | x |
| PrCl₃ 6H₂O | x | ✓ NIR | x | ✓ NIR | x | x |
| SmCl₃ | N/A | ✓ NIR | Ø | ✓ NIR | x | x |
| DyCl₃ | x | ✓ | Ø | ✓ | x | x |
| Tm(SO₃CF₃)₃ | x | ✓ | x | ✓ | x | x |
| HoCl₃ | N/A | ✓ | Ø | ✓ NIR | x | x |

Table 2 shows that complexes of HBO with various lanthanide ions are formed. As can be seen, triethylamine was generally beneficial, except in the case of dioxane as a solvent where no reaction took place.

X-Ray Structure and Photophysical Properties of the Exemplary Compounds

Figure 2:
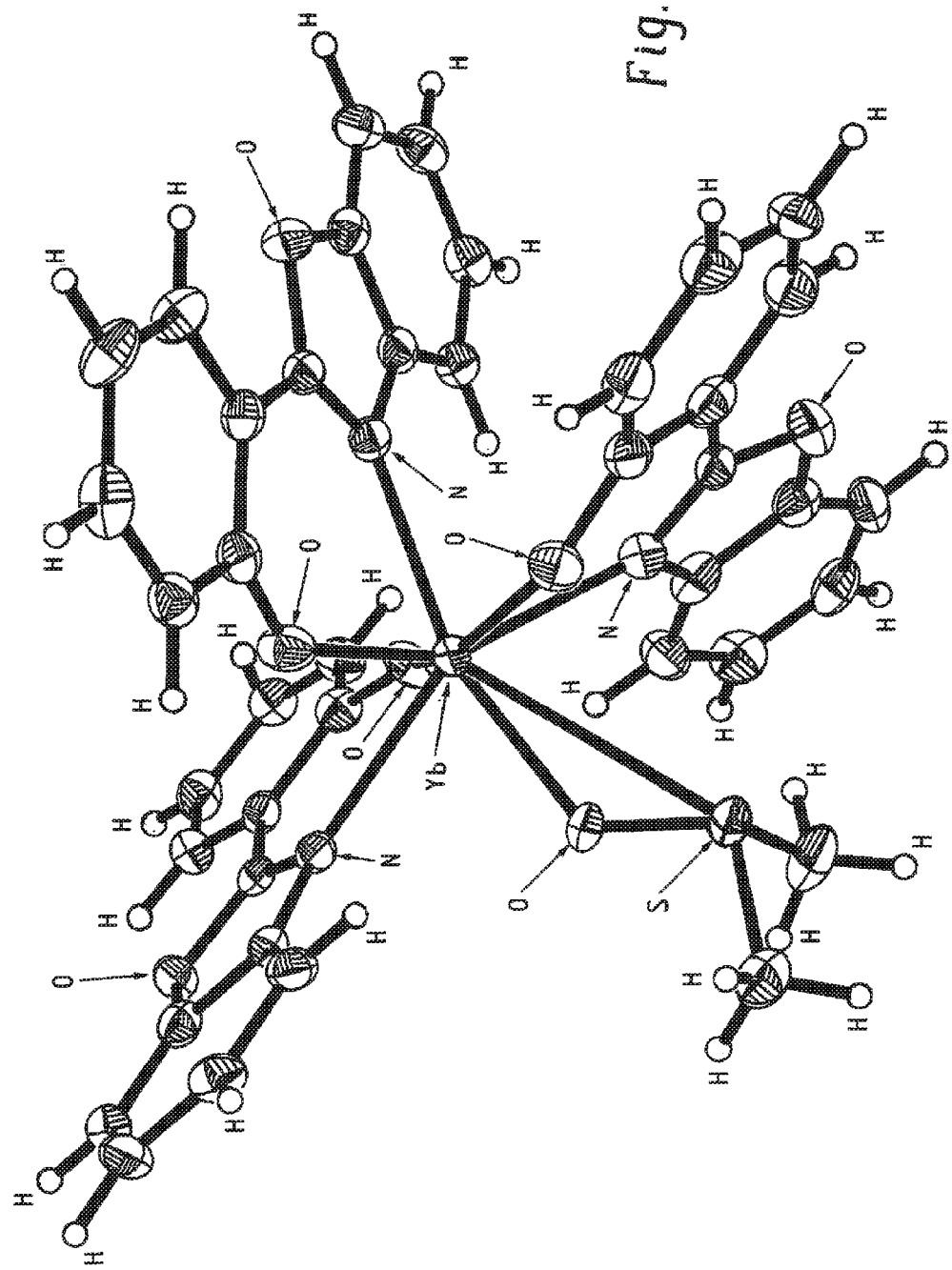
FIG. 2 illustrates an x-ray structure of a representative lanthanide complex of Yb(HBO)$_3$.DMSO.

The structure of the complex can be confirmed by x-ray analysis. FIG. 1 shows an X-ray crystal structure of Compound 1, Yb₂(HBO)₆, recrystallized from DMF. FIG. 2 depicts an X-ray crystal structure of Yb(HBO)₃.DMSO, which is the product of Compound 1, after recrystallization from DMSO solvent.

Figure 3:
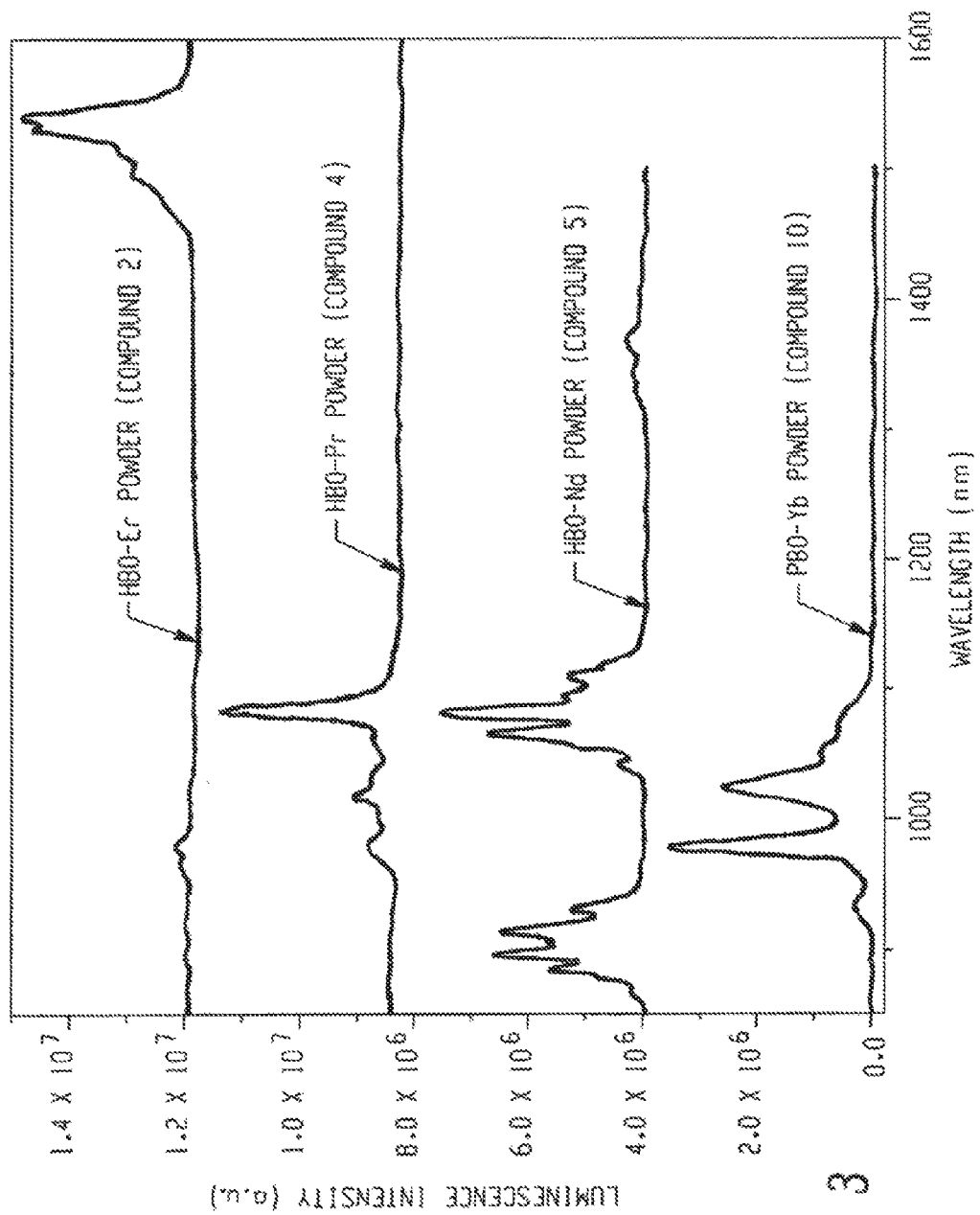
FIG. 3 shows emission spectra of HBO-coordinated lanthanide complexes in the powder form which were formed in a heterogeneous reaction scheme.

FIG. 3 shows emission spectra of various HBO-coordinated lanthanide complexes (compounds 1, 2, 4, and 5) in the powder form (Reaction Scheme 1). As can be seen, the compounds have peaks at different wavelengths in the NIR range. The spectra exhibited different characteristics of lanthanide emission, such as pure and multiplicity of spectrum peaks.

Figure 4:
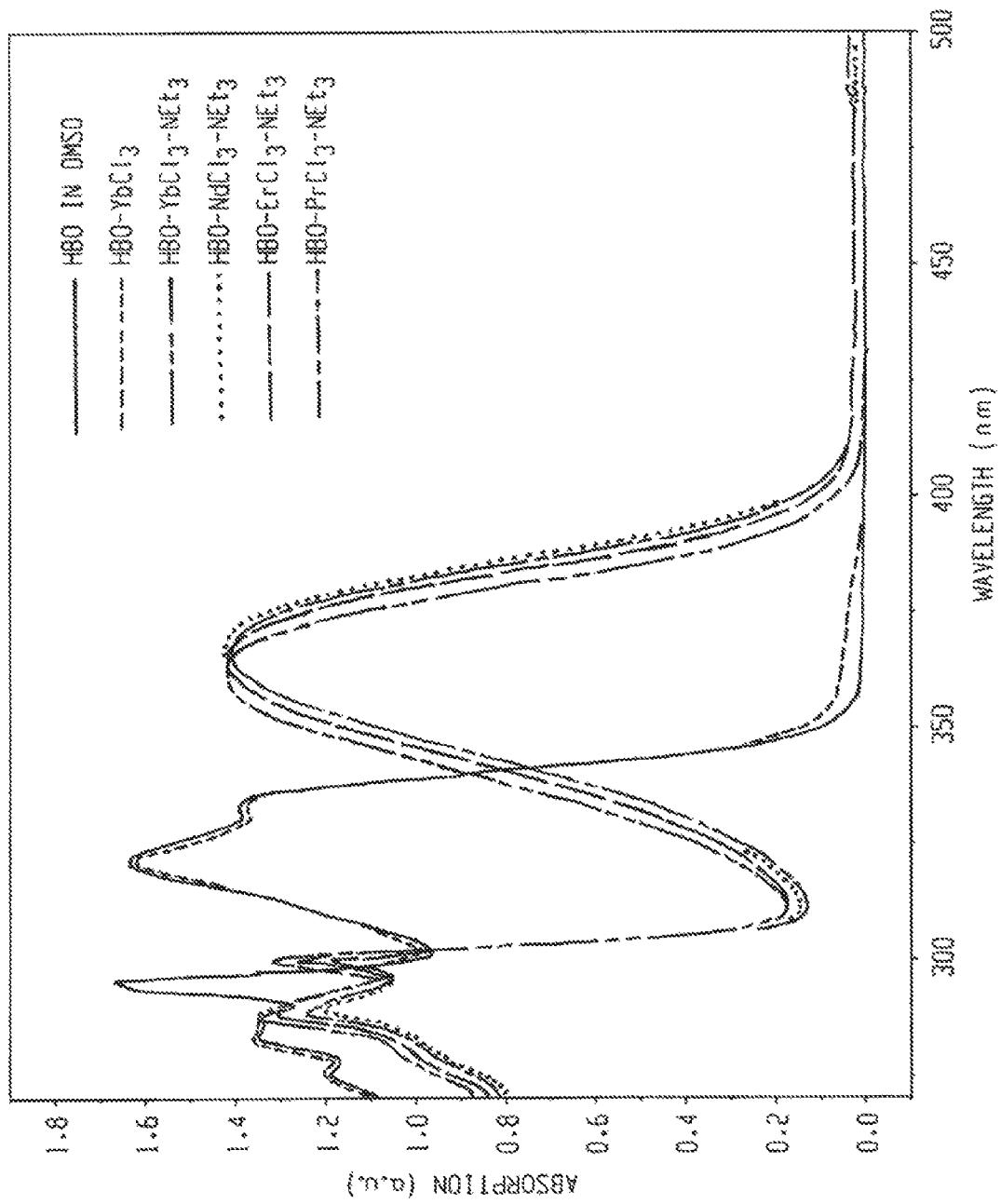
FIG. 4 shows absorption in the UV-visible range of exemplary complexes formed in situ from HBO and lanthanide ions in DMSO, with and without triethylamine.
Figure 5:
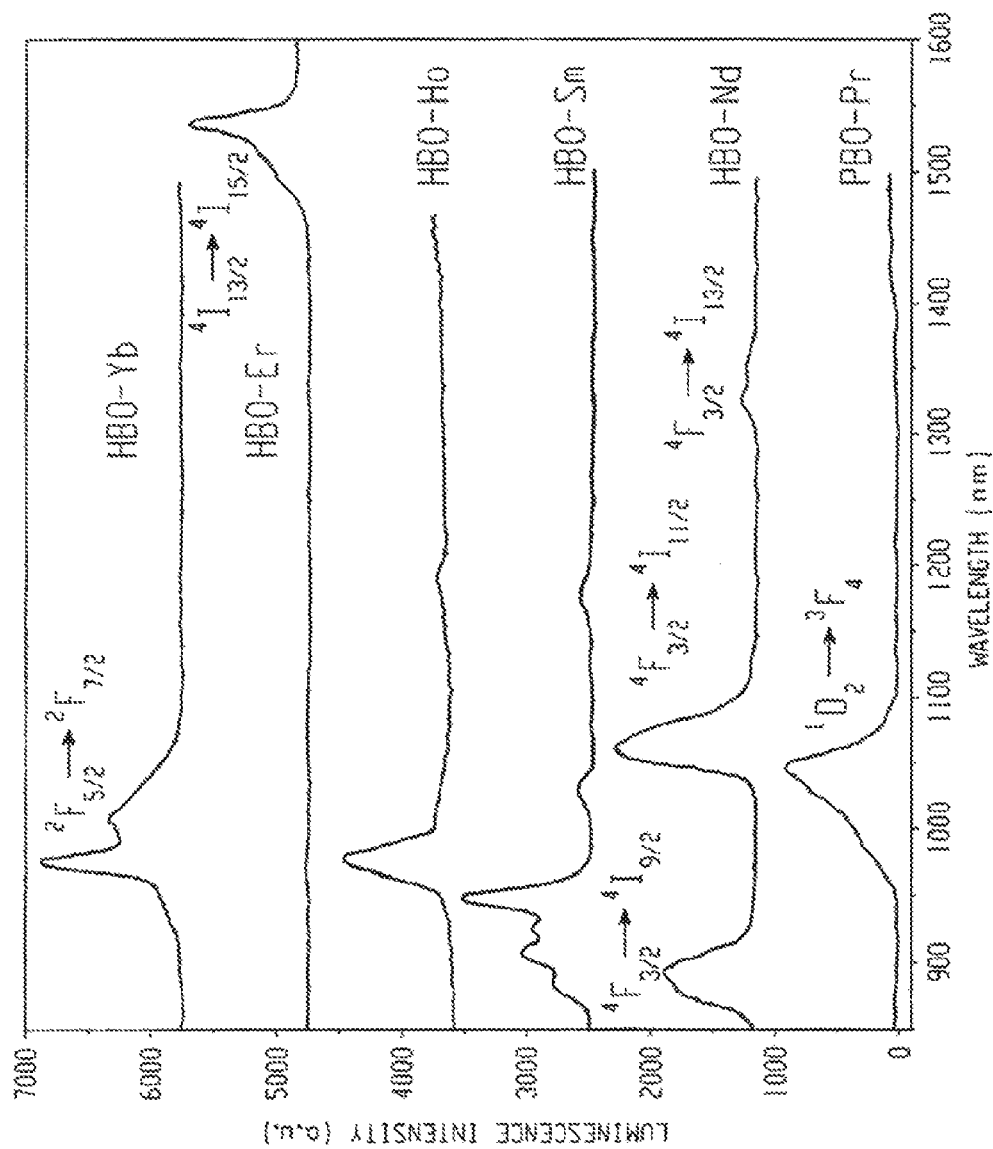
FIG. 5 shows photoluminescence spectra of HBO lanthanide complexes formed in-situ in DMSO solution in the presence of NEt$_3$.

FIG. 4 shows absorption in the UV-visible range of various complexes formed in situ from HBO and lanthanide ions in DMSO (Reaction Scheme 2), with and without triethylamine. FIG. 5 shows photoluminescence spectra of HBO lanthanide complexes formed in-situ in DMSO solution in the presence of triethylamine.

Table 3 provides a comparison of photophysics data of lanthanide complexes of benzoxazole derivatives: HBO, a ligand derived from structure 6 (Ligand 6) and a ligand derived from structure 19 (Ligand 19) formed in-situ in DMSO solution in the present of triethylamine. Maximum absorption wavelengths were detected in the UV-Visible range, and maximum emission wavelengths were detected in the NIR range, by photoluminescence.

TABLE 3

Photophysics data for lanthanide complexes of HBO, Ligand 16, and Ligand 19

| | UV-Vis, λmax (nm) | | | NIR, PL λmax, (nm) | | |
|----|----|----|----|----|----|----|
| Ln | HBO | Ligand 6 | Ligand 19 | HBO | Ligand 6 | Ligand 19 |
| Pr | 367 | 399 | 424 | 1043 | 862, 041 | 1053 |
| Nd | 368 | 400 | 425 | 893, 1059, 1329 | 895, 1060, 1332 | 891, 1061, 1335 |
| Sm | 367 | 400 | 424 | 949, 1032, 1180 | 894, 1058, 1329 | 950, 1029, 1176 |
| Dy | 367 | 399 | 425 | None | 950, 1031, 1178 | None |
| Ho | 366 | 399 | 426 | 980 | 980 | 980 |
| Er | 366 | 397 | 425 | 1541 | 1541 | 1539 |
| Tm | 365 | 397 | 424 | None | None | None |
| Yb | 363 | 394 | 424 | 979, 1012 | 980, 1014 | 980, 1012 |

Table 4 provides a comparison of similar photophysics data of lanthanide complexes of benzimidazole derivatives: HBI, a ligand derived from structure 12 (Ligand 12) and a ligand derived from structure 13 (Ligand 13), formed in-situ in DMSO solution in the presence of triethylamine.

TABLE 4

Photophysics data of lanthanide complexes of HBI, Ligand 12 and Ligand 13

| | UV, λmax (nm) | | | NIR, PL λmax, (nm) | | |
|----|----|----|----|----|----|----|
| Ln | HBI | Ligand 12 | Ligand 13 | HBI | Ligand 12 | Ligand 13 |
| Pr | 352 | 367 | 361 | 1044 | 1041 | 865, 1040 |
| Nd | 353 | 370 | 363 | 897, 1059, 1330 | 895, 1057, 1329 | 898, 1060, 1334 |
| Sm | 353 | 370 | 363 | 950, 1032, 1182 | 947, 1031, 1178 | 894, 1058, 1329 |
| Dy | 350 | 360 | 360 | 920, 1013, 1188 | None | None |
| Ho | 353 | 360 | 362 | 980, 1024 | 982 | 980, 1027, 1197 |
| Er | 352 | 359 | 361 | 1540 | 982, 1539 | 980, 1541 |
| Tm | 352 | 358 | 360 | 1203 | None | 981, 1210 |
| Yb | 351 | 356 | 360 | 979, 1015 | 982, 1020 | 982, 1027 |

Table 5 provides a comparison of photophysics data lanthanide complexes of benzothiazole derivatives: HBT, a ligand derived from structure 9 (Ligand 9) and a ligand derived from structure 10 (Ligand 10) formed in-situ in DMSO solution in the presence of triethylamine.

TABLE 5

Photophysics data of lanthanide complexes of HBT, Ligand 9 and Ligand 10

| | UV, λmax (nm) | | | NIR, PL λmax, (nm) | | |
|----|----|----|----|----|----|----|
| Ln | HBT | Ligand 9 | Ligand 10 | HBT | Ligand 9 | Ligand 10 |
| Pr | 375 | 396, 414 | 464, 489 | 1037 | 1037 | None |
| Nd | 375 | 396, 414 | 464, 491 | 891, 1059, 1329 | 894, 1058, 1329 | 892, 1060, 1332 |
| Sm | 373 | 395, 414 | 464, 490 | 947, 1031, 1176 | None | None |
| Dy | 355, 370 | 388, 405 | 463, 490 | None | None | None |
| Ho | 358, 369 | 388, 405 | 462, 490 | 982, 1021 | 981 | None |
| Er | 358, 369 | 386, 405 | 464, 491 | 978, 1541 | 980, 1539 | 1541 |

TABLE 5-continued

Photophysics data of lanthanide complexes of HBT, Ligand 9 and Ligand 10

| | UV, λmax (nm) | | | NIR, PL λmax, (nm) | | |
|---|---|---|---|---|---|---|
| Ln | HBT | Ligand 9 | Ligand 10 | HBT | Ligand 9 | Ligand 10 |
| Tm | 357, 368 | 386, 405 | 463, 490 | None | None | None |
| Yb | 357, 368 | 386, 405 | 463, 489 | 980, 1017 | 982, 1019 | 981, 1013 |

As can been seen in Tables 3-5, the emission peaks of the complexes follow certain patterns for each of the lanthanide ions and which are almost unchanged with the substitution of ligand structure. It is suggested that this is because the emission resulted from the lanthanide f orbitals which are located in the inner circle of the lanthanide atoms and thus is basically unaffected by its chelating environment. In contrast, the absorption $\lambda_{max}$ of the complexes varied drastically with the different ligand structure. The absorption spectral red-shift was observed to follow the trend of: benzothiazole>benzoxazole>benzimidazole derivatives, indicating the effect of the heteroatom in the azole unit on the complexation. In addition, the conjugation of substituted ligands also leads to the red-shift in the absorbance spectra. The impact of lanthanide ion on the absorbance was slim, but followed conventional observation, that is, the absorbance was blue-shift as radius of lanthanide ion decreased. Intramolecular Energy Transfer from Triplet State of the Ligand $L^1$ to the Associated Lanthanide Ion Without adhering to any particular theory, it is proposed that the sensitization of lanthanide ions involves an intramolecular energy transfer via the sequential process of ligand singlet→ligand triplet→lanthanide luminescent energy levels. The overall efficiency of the process is dependent on the relative positions of the lowest triplet energy level of the ligand, which can be perturbed (or adjusted) via chemical modification of the ligand structure. Only those ligands which exhibit the triplet energy level above the lanthanide luminescent energy levels are found to transfer the energy by an intramolecular process. In addition, the lifetime of the ligand triplet state also has profound effect on the efficiency of energy transfer.

Figure 6:
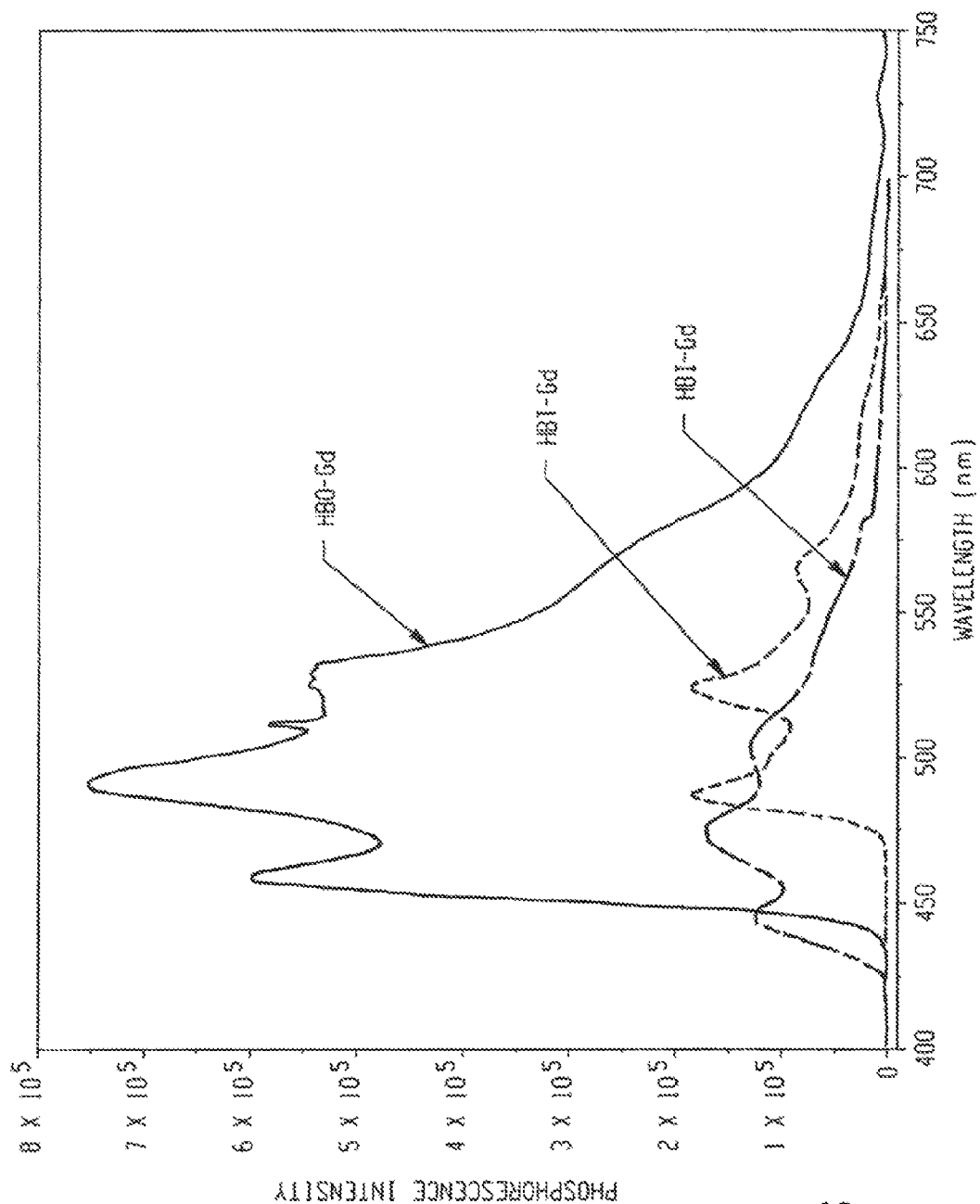
FIG. 6 shows phosphorescence spectra of HBI-, HBO-, and HBT-ligands of Gadolinium complexes in DMSO at 77K in which the different spectral positions show that the triplet-state energy levels of the attached ligands are dependent on the heteroatoms present in the heterocyclic rings.
Figure 7:
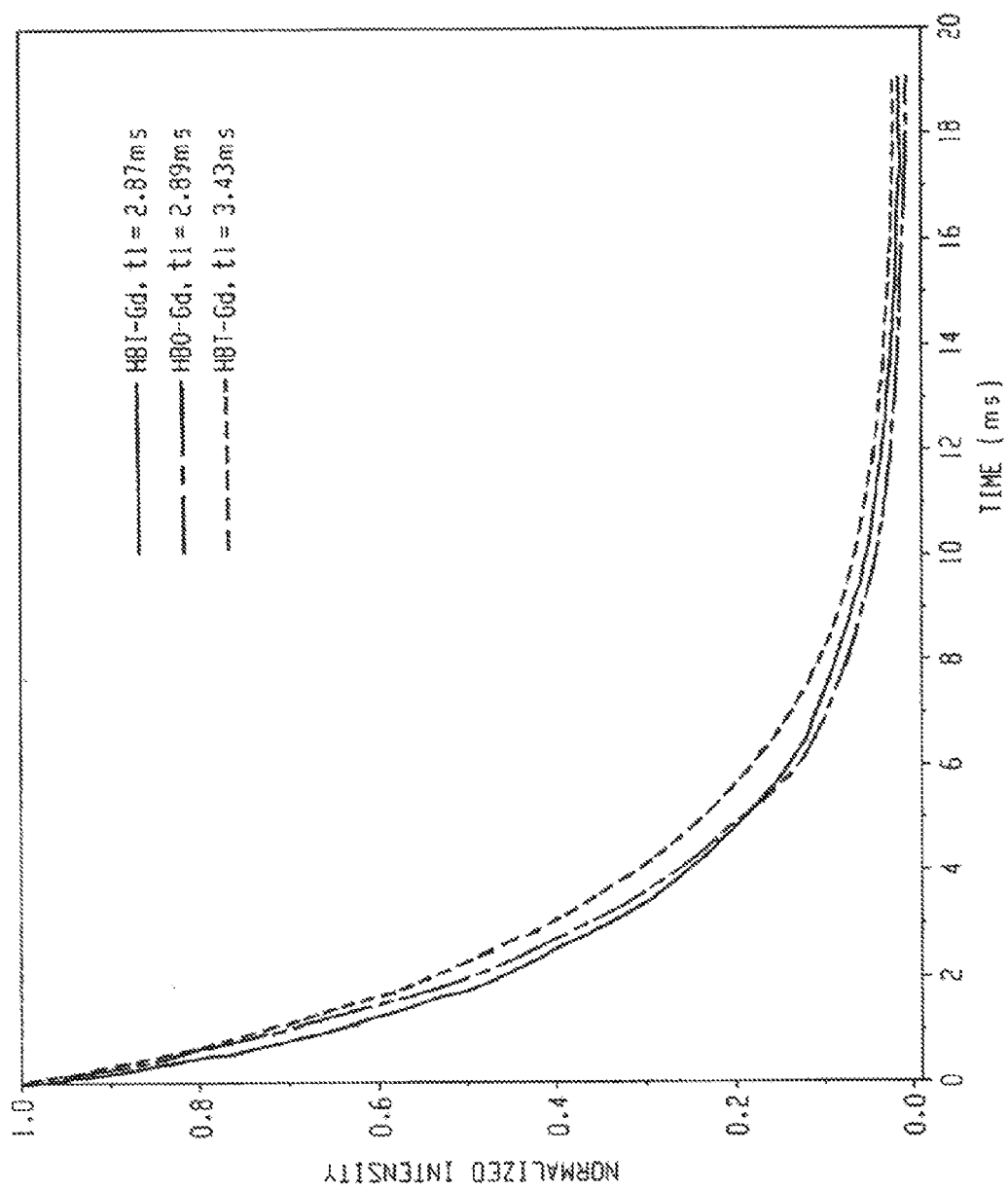
FIG. 7 shows time-resolved decay curves taken with a 1.0 ms delay of HBI-Gd, HBO-Gd and HBT-Gd complexes in DMSO at 77K (formed by a homogeneous reaction scheme), in the absence of O$_2$.
Figure 8:
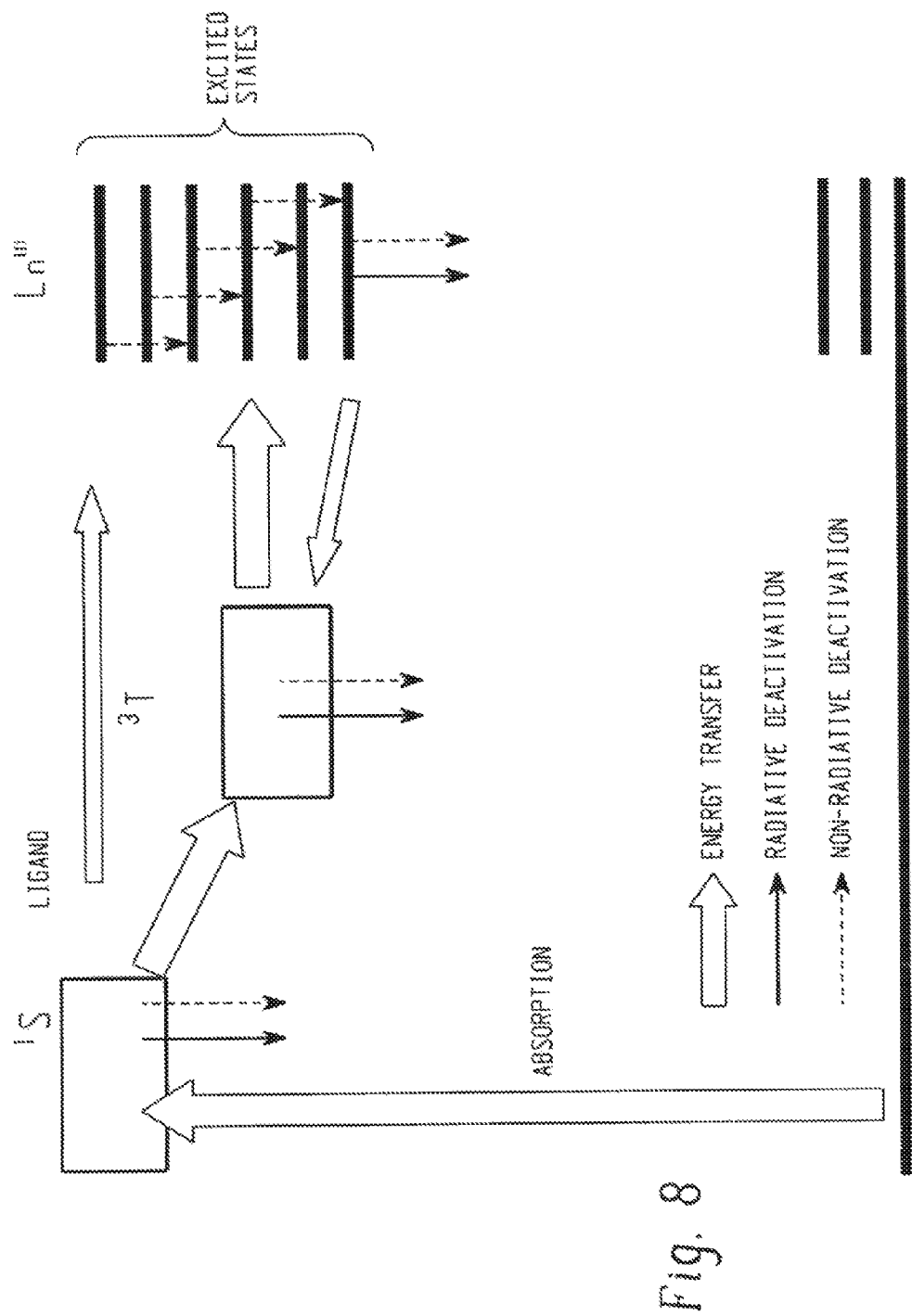
FIG. 8 is a simplified diagram showing the energy flow path during sensitization of lanthanide luminescence: (singlet excited state $^1$S)→(triplet excited state $^3$T)→(excited states of lanthanide ions Ln$^{3+}$). To achieve an efficient energy transfer, the triplet energy levels ($^3$T) are matched to the luminescence energy levels of lanthanide ions (Ln$^{3+}$)

The triplet level of a certain molecule can be enhanced and directly observed by detecting the phosphorescence of the complexes of gadolinium (Gd) due to its higher energy level that prohibits the long-lived phosphorescence from being quenched by a fast intramolecular energy-transfer process. FIGS. 6 and 7 show phosphorescence spectra and time-resolved decay curves of HBI-Gd, HBO-Gd and HBT-Gd complexes (formed by Reaction Scheme 2). The phosphorescence spectra were taken at 77K with 1.0 ms delay in DMSO solution in the absence of $O_2$. As can be seen in the FIG. 6, the triplet energy level of the three azole derivatives covered a wide range of from 23,364 cm$^{-1}$ (=428 nm) to 15,384 cm$^{-1}$ (=650 nm), which is well superimposed with the main luminescent energy levels of most lanthanide ions. HBI possesses the highest triplet energy, which accounts for its sensitization ability of all the lanthanide ions tested, followed by that of HBO and then HBT.

The phosphorescence lifetimes of the three compounds, shown in FIG. 7 are all of about the same scale (half life $t_1$ of about 3 ms). This is significant larger than that of quinolinol derivatives (half life of about 0.5 ms), which are known as ligands for the lanthanide ion sensitization. The longer lifetime of ligand triplets increases the probability of energy transfer, so does the sensitization ability. Based on the mechanism underlying the sensitization of lanthanide ions, the matched energy level and prolonged lifetime illustrates the great sensitization ability of the compounds and complexes disclosed herein.

Figure 9:
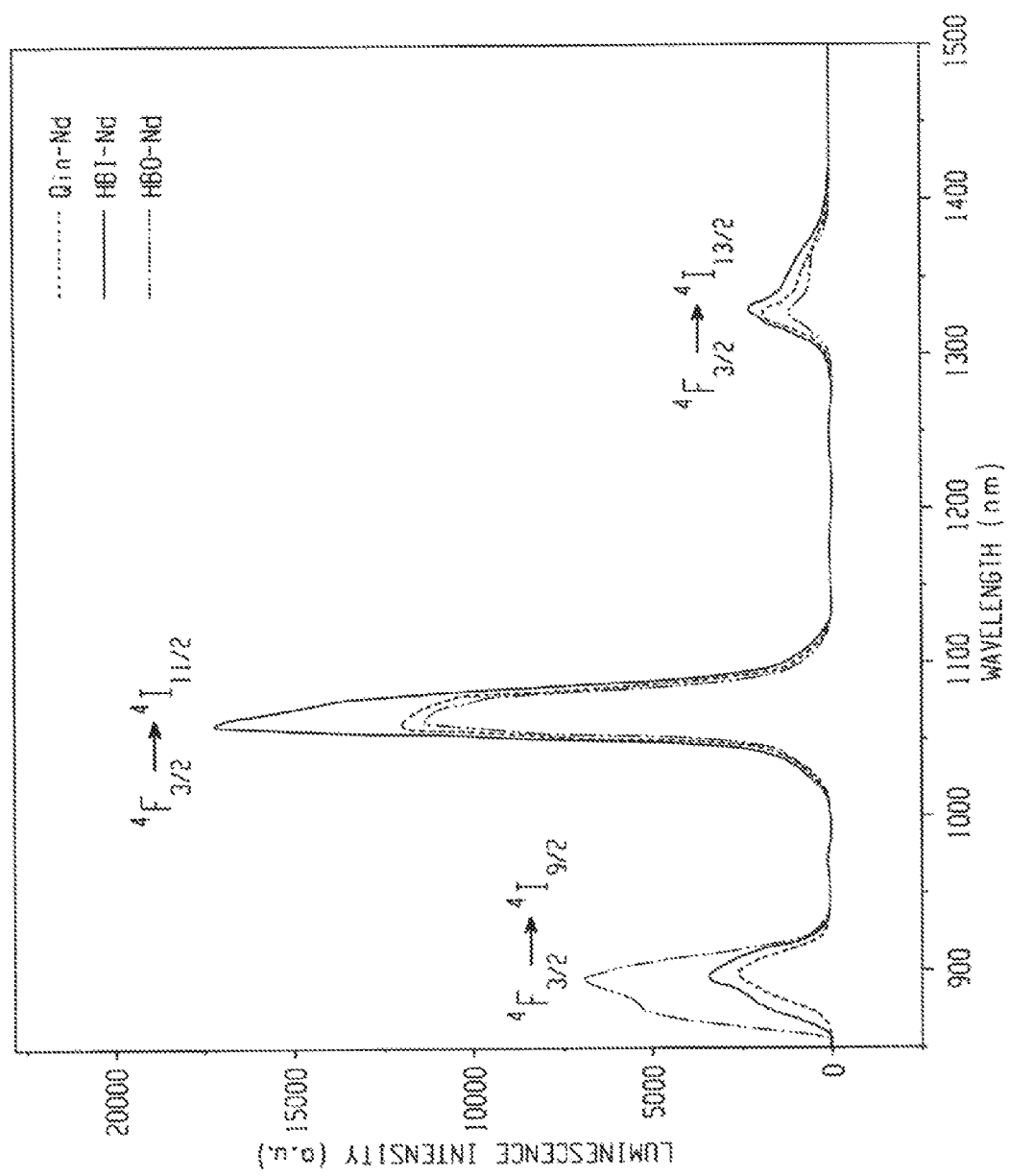
FIG. 9 illustrates luminescence intensities from Nd$^{3+}$ complexes formed in situ from HBO, HBI, and quinoline (Qin) in DMSO (1.0×10$^{-5}$M).

As an example lanthanide ion, the neodymium cation $Nd^{3+}$ gives emission lines at 887 nm and 1060 nm, corresponding to energy transitions $^4F_{3/2} \rightarrow ^4I_{9/2}$ and $^4F_{3/2} \rightarrow ^4I_{11/2}$ (shown in FIG. 5). Although the emission peak at 1060 nm is widely used in the commercial YAG laser system, the emission peak at 887 nm may play a particular role in imaging applications for the exemplary complex. By way of comparison, FIG. 9 shows the emission of $Nd^{3+}$ complexes formed in situ from HBO, HBI, and quinoline (Qin) in DMSO ($1.0 \times 10^{-5}$M). The HBO-$Nd^{3+}$ complex gives higher intensity from the $^4F_{3/2} \rightarrow ^4I_{9/2}$ transition (at ~890 nm), than that from the 8-hydroxyquinoline complex, Qin-$Nd^{3+}$. The exemplary ligands are also capable of adjusting the emission ratio between the two emission lines, with HBI-$Nd^{3+}$ showing stronger emission at 1060 nm while HBO-$Nd^{3+}$ shows stronger emission at ~887 nm. These results illustrate that the choice of heteroatom "E" in the ligand Structure 2 can have a significant impact on the NIR emissive properties of the respective lanthanide complexes.

The results demonstrate that the properties of the exemplary complexes of Reaction Schemes 1 and 2 may vary widely. This makes them applicable to a variety of applications. For diagnostic imaging of areas of lesions, fluorescent compounds absorbing and emitting in the near infrared (NIR) region, i.e. 650-900 nm, are desirable. For monitoring blood clearance or for endoscopic examination of lesions, dyes absorbing and emitting in the region of 350-950 nm, e.g. 600-900 nm, are useful.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A polydentate ligand of Structure 2:

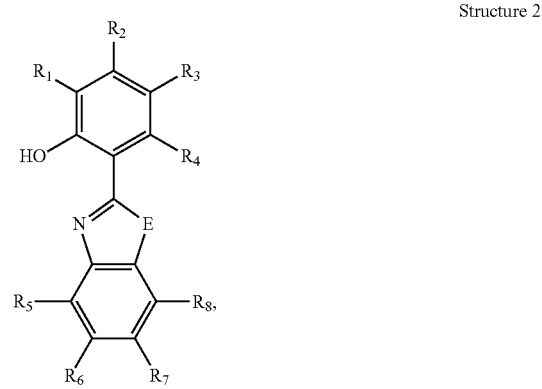

Structure 2 where:
E is a heteroatom or heteroatom-containing group; and
$R_1$ and $R_4$-$R_8$ are independently selected from the group consisting of H, —OH, —NH$_2$, and X, where X is a halide, —SO$_3$H—CO$_2$H, optionally substituted organic groups, or conjugated linking groups which link two of the polydentate ligands of Structure 2 together; $R_2$ is a substituted organic group, wherein the substituted organic group of $R_2$ is a heterocyclic group; $R_3$ is an —OH group; and at least one of $R_1$ and $R_5$ is a chelating group independently selected from the group consisting of —CO$_2$H, a dipicolyl amino group, and polyaminocarboxylic acid group, the dipicolyl amino group or polyaminocarboxylic acid group being linked through a carbon-containing bridge of from 0-2 carbon atoms.

2. The polydentate ligand of claim 1, where the heterocyclic group $R_2$ is

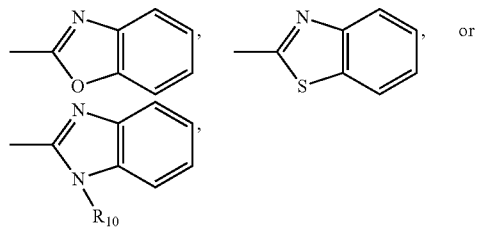

wherein $R_{10}$ is an optionally substituted $C_1$-$C_{15}$ group selected from the group consisting of alkyl, alkenyl, alkynyl, cycloalkyl, aryl, and alkylaryl groups.

3. The polydentate ligand of claim 1, wherein at least one of $R_1$ and $R_5$ is independently selected from the group consisting of:

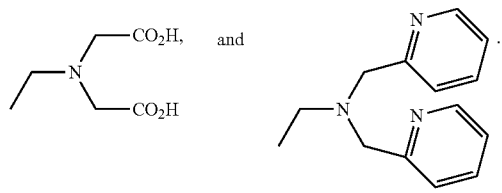 [SMILES: CCN(CC(=O)O)CC(=O)O ; CCN(Cc1ccccn1)Cc1ccccn1]

4. The polydentate ligand of claim 1, wherein E is selected from the group consisting of O, S, P, Si, B, and N—R, where R is selected from H, alkyl, and aryl groups.

5. The polydentate ligand of claim 1, where the polydentate ligand defined by the following formula:

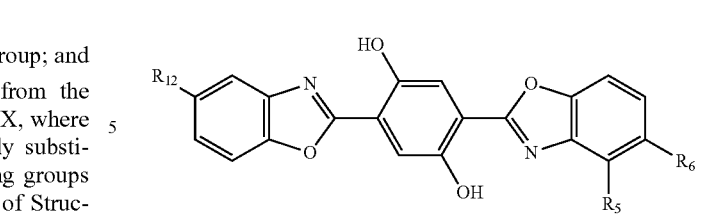

where $R_{12}$ and $R_6$ are each individually selected from the group consisting of —H and —C(CH$_3$)$_3$, and $R_5$ is selected from the group consisting of

—CO$_2$H,

[structure with N, two CO$_2$H groups]   and

[structure with N and two pyridyl groups].

6. The polydentate ligand of claim 5, where $R_{12}$ is —C(CH$_3$)$_3$.

7. The polydentate ligand of claim 5, where $R_6$ is —H.

8. The polydentate ligand of claim 5, where $R_5$ is

[structure with N and two pyridyl groups].

9. The polydentate ligand of claim 5, where $R_{12}$ is —C(CH$_3$)$_3$, $R_6$ is —H, and $R_5$ is

[structure with N and two pyridyl groups].

* * * * *